United States Patent [19]

Rasberger et al.

[11] 4,263,202

[45] Apr. 21, 1981

[54] NOVEL METAL COMPLEXES

[75] Inventors: Michael Rasberger; Samuel Evans; Paul Moser, all of Riehen, Switzerland

[73] Assignee: Ciba-Geigy Corporation, Ardsley, N.Y.

[21] Appl. No.: 923,124

[22] Filed: Jul. 10, 1978

[30] Foreign Application Priority Data

Jul. 15, 1977 [CH] Switzerland .................. 8794/77

[51] Int. Cl.$^3$ .................. C07D 401/14; C07D 401/12; C07D 401/10; C07D 413/02
[52] U.S. Cl. .................. 260/45.75 R; 260/45.75 J; 260/45.75 Q; 260/45.75 N; 260/45.75 G; 260/45.75 M; 260/45.75 W; 260/45.8 N; 260/45.8 NT; 260/45.8 NZ; 260/45.8 NE; 260/45.95 J; 542/417; 542/422; 542/424; 542/423; 542/434; 542/435; 542/436; 542/437; 542/438; 542/439; 542/440; 544/64; 544/82; 544/129; 544/130; 546/6; 546/187; 546/199; 546/207; 546/208; 546/219; 546/220; 541/221; 546/222; 546/223; 546/224; 546/226; 546/233; 546/234; 546/235; 546/236; 546/237; 546/238; 546/240; 546/242; 552/400 R

[58] Field of Search .................. 544/64, 82, 129, 130; 542/417, 424, 434, 435, 436, 437, 438, 439, 440; 260/293.64, 293.78, 270 K, 293.77, 293.73, 293.59, 293.82, 45.95 J, 45.75 J, 45.75 Q, 45.75 N, 45.75 G, 45.75 M, 45.75 W, 45.75 R, 45.8 N, 45.8 NT, 45.8 NZ, 45.8 NE; 546/6, 187, 199, 208, 207, 219, 221, 223, 224, 220, 222, 226, 234, 235, 239, 237, 240, 236

[56] References Cited

U.S. PATENT DOCUMENTS

| | | | |
|---|---|---|---|
| 3,464,953 | 9/1969 | Newland | 260/45.75 N |
| 3,636,023 | 1/1972 | Murray | 260/439 R |
| 3,745,163 | 7/1973 | Holt et al. | 260/293.77 |
| 3,847,930 | 12/1974 | Randell | 546/344 |
| 3,879,396 | 4/1975 | Ramey et al. | 260/270 |
| 3,891,685 | 6/1975 | Hari et al. | 260/270 K |
| 3,892,750 | 7/1975 | Frey | 260/270 K |
| 3,948,852 | 4/1976 | Rasberger et al. | 260/45.75 N |
| 3,992,390 | 11/1976 | Holt et al. | 260/293.82 |
| 4,001,181 | 1/1977 | Ramey et al. | 260/45.75 N |
| 4,026,866 | 5/1977 | Rasberger et al. | 260/45.75 N |
| 4,052,361 | 10/1977 | Susi et al. | 260/293.77 |

FOREIGN PATENT DOCUMENTS 2625967 4/1977 Fed. Rep. of Germany .

OTHER PUBLICATIONS

Medzhidov et al., Chem. Abs. 71, 49713q (1969).
Medzhidov et al., Iz. Akad Naak SSR 3, 698–700 (1969).

*Primary Examiner*—Mark L. Berch
*Attorney, Agent, or Firm*—Harry Falber

[57] ABSTRACT

Metal phenolates having at least one piperidinyl group sterically hindered on the nitrogen atom are suitable as additives for organic material.

10 Claims, No Drawings

NOVEL METAL COMPLEXES

The present invention relates to novel metal complexes of metal cations having a double or triple charge with a chelate-forming anion containing phenolate groups, the preparation of these complexes and their use as light stabilisers in organic material, and also to the organic material protected with the aid of these complexes.

Metal complexes with sterically hindered amines and anions having a single charge have been described as stabilisers for synthetic polymers in German Offenlegungsschrift No. 2,625,967. These complexes are mixtures of metal salts and sterically hindered amines.

Novel metal chelate complexes have now been found which are distinguished by a good light-stabilising action and good stability to extraction and have a good compatibility in polymers.

The novel metal complexes are of the general formula I $$[M^{q\oplus}][L^{r\ominus}]_{(q-s)/r}[B^{\ominus}]_s \cdot m\,A \qquad (I)$$

in which M is a metal ion having a double or triple positive charge, q is 2 or 3 and L is a t-dentate chelate-forming anion which contains 1 or 2 phenolate groups and which contains at least one group of the formulae IIa or IIb

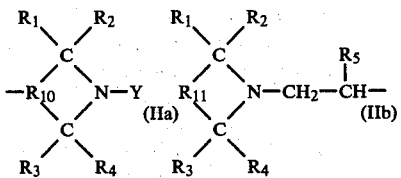

in which t is 2, 3 or 4 and $R_1$, $R_2$, $R_3$ and $R_4$ independently of one another are alkyl, or $R_1$ and $R_3$ together are alkylene, or, independently of one another, $R_1$ and $R_2$, or $R_3$ and $R_4$, together are alkylene or azaalkylene, and $R_5$ is hydrogen, methyl or phenyl and Y is hydrogen, oxyl, alkyl, alkenyl, alkynyl, alkoxyalkyl, aralkyl, 2,3-epoxypropyl, an aliphatic acyl group or one of the groups $-CH_2COOR_6$, $-CH_2-CH(R_7)-OR_8$, $-COOR_9$ or $-CONHR_9$, in which $R_6$ is alkyl, alkenyl, phenyl, aralkyl or cycloalkyl and $R_7$ is hydrogen, methyl or phenyl and $R_8$ is hydrogen or an aliphatic or aromatic or an araliphatic or alicyclic acyl group, in which the aromatic part can be unsubstituted or substituted by chlorine, alkyl, alkoxy and/or hydroxyl, and $R_9$ is alkyl, cyclohexyl, phenyl or benzyl and $R_{10}$ is a trivalent organic radical and $R_{11}$ is a divalent organic radical, $R_{10}$ and $R_{11}$ completing the N-containing ring to give a 5-membered, 6-membered or 7-membered ring, and r is 1 or 2 and equal to the number of coordinatively bonded phenolate anions in the molecule and B is a ligand having a single negative charge and s is an integer from 0 to 2, and the sum $(q-s)/r+s$ must equal q, and m is an integer from 0 to 3, the sum $t \cdot [(p-s)/R]+s+m$ being equal to the coordination number of the metal ion M, and A is $H_2O$ or an amine of the formula III

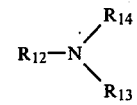

in which $R_{12}$ is substituted or unsubstituted alkyl, cycloalkyl, aryl or aralkyl, a substituted or unsubstituted aminoalkyl group or a piperidinyl group and $R_{13}$ is hydrogen or substituted or unsubstituted alkyl or cycloalkyl, a substituted or unsubstituted aminoalkyl group or a piperidinyl group, or $R_{12}$ and $R_{13}$ together with the N atom form a pyrrolidine, piperidine or morpholine ring which is substituted by alkyl groups or is unsubstituted, and $R_{14}$ is hydrogen or substituted or unsubstituted alkyl.

As alkyl, $R_1$, $R_2$, $R_3$ and $R_4$ independently of one another are, especially, alkyl having 1–6 C atoms, preferably ethyl and very particularly methyl.

As alkylene, $R_1$ and $R_3$ together are, especially, alkylene having 1–6 C atoms, in particular methylene or ethylene.

$R_1$ and $R_2$, or $R_3$ and $R_4$, together as alkylene are especially straight-chain or branched alkylene having 4–8 C atoms, in particular pentamethylene, and as azaalkylene are, especially, straight-chain or branched azaalkylene having 4–16, and in particular 4–10, C atoms, which can be substituted on the N atom, especially by a monovalent radical Y and in particular by alkyl, such as alkyl having 1–6 C atoms, especially methyl, but which, especially, is substituted on the N atom, such as 3-aza-pentamethylene and especially 2,2,4,4-tetramethyl-3-aza-pentamethylene, 2,2,3,4,4-pentamethyl-3-aza-pentamethylene or the N-oxyl of 2,2,4,4-tetramethyl-3-aza-pentamethylene. Preferably, only one of the pairs $R_1/R_2$ and $R_3/R_4$ is alkylene or azaalkylene and the other is in each case alkyl, and in particular all of the radicals $R_1$, $R_2$, $R_3$ and $R_4$ are alkyl. $R_5$ is especially hydrogen or methyl.

As alkyl, Y is especially alkyl having 1–12 C atoms, preferably α-unbranched, and in particular having 1–4 C atoms, and very particularly is methyl.

As alkenyl, Y is especially alkenyl having 3–12, and in particular having 3–6, C atoms, such as allyl, methallyl, n-hex-3-enyl, n-oct-4-enyl and n-undec-10-enyl.

As alkynyl, Y is especially alkynyl having 3–6 C atoms, such as propargyl, n-but-1-ynyl, but-2-ynyl and n-hex-1-ynyl.

If Y is alkoxyalkyl, the alkyl part can contain 1–3 C atoms and the alkoxy part can consist of 1–18 C atoms, as, for example, in methoxymethyl, ethoxymethyl, 2-methoxyethyl, 2-ethoxyethyl, 2-n-butoxyethyl, 3-n-butoxyethyl, 2-octoxyethyl or 2-octadecyloxyethyl. Compounds in which Y is an alkoxy group having 2–5 C atoms are to be mentioned in particular.

As aralkyl, Y is aralkyl having 7–9 C atoms, for example benzyl or α-phenylethyl.

As an aliphatic acyl group, Y is especially an aliphatic acyl group having 1–4 C atoms, for example formyl, acetyl, acryloyl or crotonyl, especially acetyl.

If Y is the group $-CH_2COOR_6$, $R_6$ is $C_1-C_{12}$ alkyl, for example methyl, ethyl, isopropyl, n-butyl, isobutyl, t-butyl, isopentyl, n-octyl, n-decyl or n-dodecyl; preferably, $R_6$ is $C_1-C_4$ alkyl, or $R_6$ is $C_3-C_6$ alkenyl, for example allyl, 2-butenyl or 2-hexenyl, or $C_7-C_8$ aralkyl, for example benzyl or α-phenylethyl, or, finally, $C_5-C_7$ cycloalkyl, especially cyclohexyl.

If Y is the group —CH$_2$—CH(R$_7$)—OR$_8$, R$_7$ is hydrogen, methyl or phenyl, especially hydrogen. As an aliphatic C$_1$–C$_{18}$ acyl radical, R$_8$ is, for example, formyl, acetyl, propionyl, butyryl, octanoyl, dodecanoyl, stearoyl or acryloyl. As an aromatic C$_7$ acyl radical, R$_8$ is benzoyl and as an araliphatic C$_8$–C$_9$ acyl radical R$_8$ is cinnamoyl, phenylacetyl or phenylpropionyl. The aromatic part is unsubstituted or substituted by chlorine or C$_1$–C$_4$ alkyl, such as methyl, ethyl, n-propyl or t-butyl, or by C$_1$–C$_8$ alkoxy, such as methoxy, ethoxy, butoxy or octoxy, and/or hydroxyl. Substituted aromatic acyl groups are, for example, chlorobenzoyl, toluoyl, isopropylbenzoyl, 2,4-dichlorobenzoyl, 4-methoxybenzoyl, 3-butoxybenzoyl, 2-hydroxybenzoyl or 3,5-di-t.-butyl-4-hydroxybenzoyl. An araliphatic substituted acyl group is, for example, β-(3,5-di-t.-butyl-4-hydroxyphenyl)-propionyl. If R$_8$ is an alicyclic C$_6$–C$_9$ acyl group, this can be cyclohexylcarbonyl or 2,4-dimethylcyclohexylcarbonyl. Hydrogen is also a preferred meaning of R$_8$.

If Y is the group —COOR$_9$, R$_9$ is C$_1$–C$_{12}$ alkyl, for example methyl, ethyl, isobutyl, t-butyl, n-hexyl, n-octyl, n-decyl or n-dodecyl. Alkyl groups having 1–4 C atoms are preferred as R$_9$.

If Y is —CONHR$_9$, R$_9$ is especially cyclohexyl or phenyl.

IF A is an amine of the formula III, the substituents R$_{12}$, R$_{13}$ and R$_{14}$ therein are, for example, C$_1$–C$_{18}$ alkyl, such as methyl, ethyl, isopropyl, sec.-butyl, n-hexyl, n-octyl, n-decyl, n-dodecyl or n-octadecyl, and preferably C$_1$–C$_8$ alkyl.

If the alkyl is substituted alkyl, this is intended to signify, especially, C$_1$–C$_{18}$ hydroxyalkyl, such as 1-hydroxyethyl, 1-hydroxypropyl, 1-hydroxy-1-methylethyl, 3-hydroxypentyl or 1-hydroxy-2-methyl-ethyl, and preferably C$_1$–C$_6$ hydroxyalkyl.

R$_{12}$ and R$_{13}$ can also be C$_5$–C$_{12}$ cycloalkyl, which can be, for example, cyclopentyl, cyclohexyl, 4-methylcyclohexyl or 4-tert.-butylcyclohexyl. R$_{12}$ can also be C$_6$–C$_{18}$ aryl, which can be, for example, phenyl, tolyl, xylyl, tert.-butylphenyl or dodecylphenyl. As aralkyl, R$_{12}$ can be C$_7$–C$_{20}$ aralkyl and is, for example, benzyl, 4-methylbenzyl, 4-t.-butylbenzyl or 4-dodecylbenzyl, especially benzyl.

If R$_{12}$ and R$_{13}$ are a substituted or unsubstituted aminoalkyl group, this is, especially, an aminoalkyl group substituted by a piperidinyl group, for example an aminoalkyl group of the formula IIc

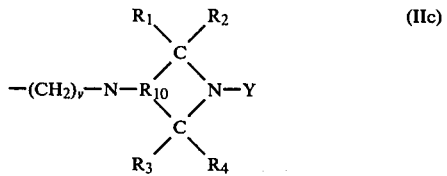

(IIc)

in which R$_1$, R$_2$, R$_3$, R$_4$, R$_{10}$ and Y are as defined above and v is an integer from 1 to 8.

If R$_{12}$ and R$_{13}$ are a piperidinyl group, this is preferably a piperidinyl group of the formula (IIa), in which R$_{10}$ is a trivalent radical

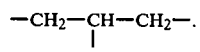

R$_{12}$ and R$_{13}$, together with the N atom of the ligand A, can form a pyrrolidine, piperidine or morpholine ring which is substituted by alkyl groups or is unsubstituted. In this case, the ring can be, for example, a 2,5-dimethylpyrrolidine, 4-methylpiperidine, 2,2,6,6-tetramethylpiperidine, 2,6-dimethylmorpholine, pyrrolidine, piperidine or morpholine ring, especially a 2,2,6,6-tetramethylpiperidine ring.

Thus, according to the definition, the ligand A is a primary, secondary or tertiary amine which is able to form a complex with the metal chelates indicated above. Examples of such amines are: n-butylamine, n-dodecylamine, β-ethylhexylamine, benzylamine, 4-octylbenzylamine, dibutylamine, dicyclohexylamine, dioctadecylamine, morpholine, 2,2,6,6-tetramethylpiperidine, N-ethylaniline, tri-n-octylamine, N,N-dimethylaniline, N,N-dimethyl-cyclohexylamine, N-ethylpiperidine, N-methylpyrrolidine, dibenzylpropylamine, N-benzyl-2,5-dimethylpyrrolidine, 4-dimethylamino-2,2,6,6-tetramethylpiperidine, 4-dimethylamino-1,2,2,6,6-pentamethylpiperidine, N,N'-methyl-N,N'-(1,2,2,6,6-pentamethyl-4-piperidyl)-ethylenediamine, hydroxyethylamine, di-(hydroxyethyl)amine, tri-(hydroxyethyl)-amine, tri-(2-hydroxy-propyl)-amine, N-phenyl-N,N-di-(hydroxyethyl)-amine or hydroxypropyl-amine.

The complexes, according to the invention, of the formula I contain, per mol of metal M$^{q+}$, 0 to 3 mols of the amine ligand A, which can be entirely or partly replaced by water. The molar proportion expressed by m in the formula I is thus made up of the sum of m' mols of amine ligand and m" mols of water; the molar proportions expressed by m' and m" do not need to be an integer. Preferred complexes are those which have a low water content, since these dissolve in nonpolar polymers better than do more highly hydrated complexes. m' thus assumes approximately the value of m.

A cation M of the valency q is, for example, a cation of the series Mg$^{2+}$, Ca$^{2+}$, Sr$^{2+}$, Ba$^{2+}$, Zn$^{2+}$, Cd$^{2+}$, Al$^{3+}$, Sn$^{2+}$, Cr$^{3+}$, Co$^{2+}$ and Ni$^{2+}$, an oxo complex of metal ions, especially VO$^{2+}$ and MoO$_2$$^{2+}$, or a tin-alkyl ion of the formula (R*)$_2$Sn$^{2+}$ or (CH$_2$CH$_2$COOR*)$_2$Sn$^{2+}$, in which R* is C$_1$–C$_8$ alkyl, but especially ethyl, n-propyl or n-octyl and in particular n-butyl, especially Ca$^{2+}$, Mg$^{2+}$, Zn$^{2+}$, Co$^{2+}$ and in particular Ni$^{2+}$ or Al$^{3+}$. The coordination numbers of these cations are known to those skilled in the art and are 4 or 6, depending on the metal.

q is 2 or 3, especially 2.

r is 1 or 2 and corresponds to the number of phenolate anions in the ligand L. Thus, if a ligand molecule contains several phenolic —OH groups, whether or not all of the phenolic OH groups are deprotonated, and thus contribute to the total charge r$^-$ on the ligand L, depends on the corresponding stability constants and the ratio M/1.

t indicates the detentation of the ligand L as 2, 3 and 4, i.e. t describes the number of donor atoms in the molecule which enter into direct interaction with the metal centre M$^{q+}$. 2-, 3- or 4-dentate ligands can be used for the set object and the metal complexes formed are uncharged.

The chelate-forming agent L must meet the condition that it contains at least one of the groups IIa or IIb. The meaning of the symbols R$_{10}$ and R$_{11}$ is then such that the groups IIa and IIb are, for example, derivatives of pyrrolidine, imidazolidine, 1,4-diazacycloheptanone, piperazine, 1-aza-4-thiacyclohexane or dipiperidyl and in particular of piperidine. Amongst the numerous piperidines, those to be mentioned are not only the simple piperidines substituted in the 4-position, but also spiro compounds, such as 1-oxa-3,8-diaza-spiro[4,5]-decanes (piperidine-spirooxazolidines), 1-oxa-6-aza-spiro[2,5]-octanes (piperidine-spiro-oxiranes), 1,4-dioxa-8-aza-spiro[4,5]-decane and 1,5-dioxa-9-azaspiro[5,5]-undecane, and also the analogous 1-thia and 4-aza compounds of the two last-mentioned piperidine-spiro-ketals, and in particular 1,3,8-triazaspiro[4,5]-decanes (piperidine-spirohydantoins).

Metal complexes which have proved particularly suitable are those of the formula I in which $L^{r+}$ is a 2-, 3- or 4-dentate chelate-forming agent selected from the category consisting of the groups IVa, IVb and IVc

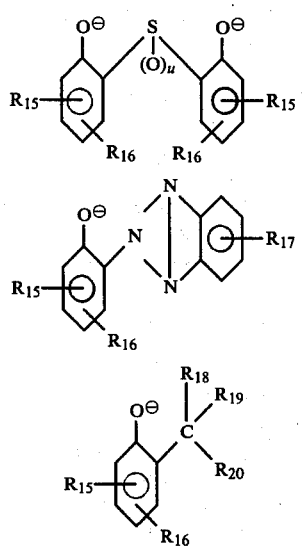

in which u is 0, 1 or 2 and r is as defined above and $R_{15}$ and $R_{16}$ independently of one another are hydrogen, $C_1$-$C_{18}$ alkyl, which can be unsubstituted or substituted by a group Va, Vb or Vc:

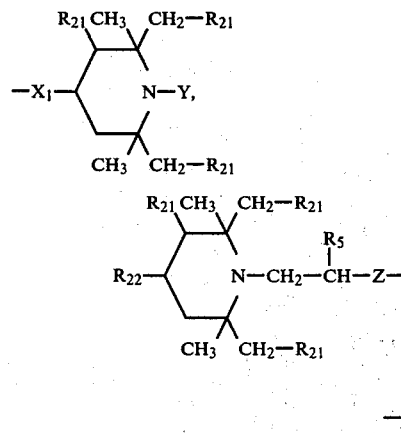

or a group Vc, or a group of the formula VI

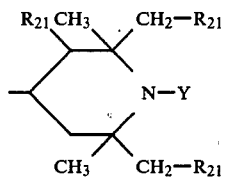

in the p-position, halogen or a radical —$OR_{24}$, or $R_{15}$ and $R_{16}$ together are a 1,3-butadiene-1,4-diyl radical, and $R_5$ and Y are as defined and $X_1$ and $X_2$ independently of one another are —O— or

and $R_{21}$ is hydrogen or $C_1$-$C_8$ alkyl and $R_{22}$ is hydrogen or a group —$X_1R_{26}$, in which $X_1$ is as defined above, and Z is —O— or

and $R_{23}$ is $C_1$-$C_{18}$ alkyl, $C_3$-$C_6$ alkenyl, $C_3$-$C_4$ alkynyl, $C_5$-$C_7$ cycloalkyl, $C_6$-$C_{10}$ aryl, $C_7$-$C_{14}$ aralkyl, $C_7$-$C_{14}$ alkylphenyl or a group of the formula VI, and $R_{24}$ is hydrogen or $C_1$-$C_8$ alkyl, $C_5$-$C_7$ cycloalkyl, $C_6$-$C_{14}$ aryl, $C_7$-$C_{14}$ aralkyl or $C_2$-$C_{12}$ alkenyl which are unsubstituted or substituted by a group of the formula Vc; or $R_{24}$ is an aliphatic $C_1$-$C_{18}$ acyl group, aromatic $C_7$ acyl group, araliphatic $C_8$-$C_9$ acyl group or alicyclic $C_6$-$C_9$ acyl group, which is unsubstituted or substituted by chlorine, $C_1$-$C_8$ alkyl, $C_1$-$C_8$ alkoxy, a group Vc and/or hydroxyl, and $R_{25}$ is hydrogen, $C_1$-$C_{18}$ alkyl, which can be unsubstituted or substituted by a group of the formula Vc, or $C_3$-$C_6$ alkenyl, $C_3$-$C_6$ alkenyl, $C_3$-$C_4$ alkynyl, $C_5$-$C_7$ cycloalkyl, $C_6$-$C_{10}$ aryl, $C_7$-$C_{14}$ aralkyl, a group of the formula $CH_2$—$CH(R_5)$—$OR_{26}$ or a group of the formula VI, and $R_{26}$ is hydrogen, $C_1$-$C_{18}$ alkyl, $C_3$-$C_6$ alkenyl, cyclohexyl, benzyl or an aliphatic $C_1$-$C_{18}$ acyl group, aromatic $C_7$ acyl group, araliphatic $C_8$-$C_9$ acyl group alicyclic $C_6$-$C_9$ acyl group, which is unsubstituted or substituted by chlorine, $C_1$-$C_8$ alkyl, $C_1$-$C_8$ alkoxy and/or hydroxyl, and $R_{17}$ is hydrogen, $C_1$-$C_{18}$ alkyl, halogen, a group —$OR_{24}$ or a group of the formula Vc and $R_{18}$ is a group —$N(R_{25})R_{27}$ and $R_{19}$ is hydrogen, or $R_{18}$ and $R_{19}$ together are =O or =$NR_{27}$, and $R_{20}$ is hydrogen, $C_7$-$C_{14}$ aralkyl, $C_7$-$C_{14}$ alkylphenyl, or $C_1$-$C_{18}$ alkyl, $C_2$-$C_{12}$ alkenyl, $C_5$-$C_{12}$ cycloalkyl or $C_6$-$C_{14}$ aryl, which are unsubstiuted or substituted by a group of the formula Vc, or, if $R_{18}$ and $R_{19}$ together are =O, $R_{20}$ is a group of the formula Va; or $R_{20}$ is also a group of the formula VII

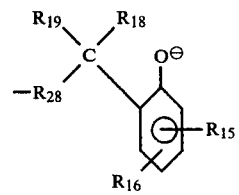

in which $R_{15}$, $R_{16}$, $R_{18}$ and $R_{19}$ are as defined above and $R_{28}$ is $C_1$-$C_{12}$ alkylene, butenylene, $C_6$-$C_{10}$ arylene or diphenylene, and $R_{27}$ is hydrogen, $C_7$-$C_{14}$ aralkyl, $C_7$-$C_{14}$ alkylphenyl, hydroxyl, or $C_1$-$C_{18}$ alkyl, $C_2$-$C_{12}$ alkenyl, $C_5$-$C_{12}$ cycloalkyl or $C_6$-$C_{14}$ aryl, which are unsubstituted or substituted by a group of the formula Vc, or a group of the formula VI, or a group of the formula —$CH_2$—$CH(R_5)$—$OR_{26}$; or $R_{27}$ is also a group of the formulae VIIIa or VIIIb

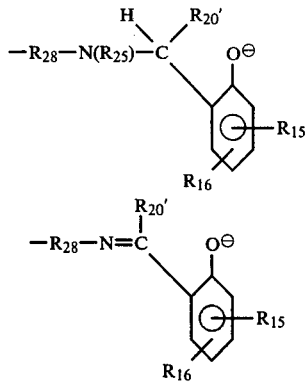

in which $R_{20}'$ has the meaning defined for $R_{20}$ with the exception of the groups of the formula VII, and $R_{15}$, $R_{16}$, $R_{25}$ and $R_{28}$ are as defined above.

The substituents mentioned in the above formulae IVa, IVb, IVc, Va, Vb, Vc, VI, VII, VIIIa and VIIIb are, for example, as defined below:

$R_5$ and Y are as defined above.

u is 0, 1 or 2, especially 0.

If $R_{15}$ and $R_{16}$ independently of one another are $C_1$-$C_{18}$ alkyl, this can be, for example, methyl, ethyl, iso-propyl, n-butyl, t-butyl, amyl, n-hexyl, n-octyl, t-octyl, n-decyl, n-dodecyl, n-octadecyl or 2-ethyl-hexyl. Preferred alkyl groups are those having 1-5 C atoms. The alkyl groups can be substituted by a group of the formulae Va, Vb or Vc, preferably Va or Vc; in this case alkyl groups having 1-4 C atoms are preferred. Preferred compounds of the formula I are those in which at most one of the radicals $R_{15}$ and $R_{16}$ is substituted by a group of the formula Va, Vb or Vc. The radicals $R_{15}$ or $R_{16}$ can also be a group Vc.

One of the radicals $R_{15}$ and $R_{16}$ can also be a group of the formula VI. For reasons of synthesis, this group must be in the p-position relative to the phenolate oxygen.

If $R_{15}$ and $R_{16}$ are halogen, this can be chlorine or bromine, especially chlorine.

$R_{15}$ and $R_{16}$ are preferably also hydrogen or —$OR_{24}$.

As $C_1$-$C_{18}$ alkyl, $R_{17}$ is, for example, methyl, ethyl, propyl, butyl, n-hexyl, n-octyl, n-decyl, n-dodecyl or n-octadecyl, and alkyl groups having 1-12 C atoms are preferred.

As halogen, $R_{17}$ is especially chlorine.

Compounds in which $R_{17}$ is hydrogen, —$OR_{24}$ and especially a group of the formula Vc are also preferred.

If $R_{20}$ and $R_{27}$ are $C_7$-$C_{14}$ aralkyl, this can be, for example, benzyl, α-phenylethyl or 2-phenylpropyl, especially benzyl.

If $R_{20}$, $R_{24}$, $R_{25}$ and $R_{27}$ are $C_1$-$C_{18}$ alkyl, this signifies, for example, methyl, ethyl, isio-propyl, n-butyl, t-butyl, amyl, n-hexyl, n-octyl, t-octyl, n-decyl, n-dodecyl or n-octadecyl. Amongst these groups, alkyl groups having 1-12 C atoms are preferred. Further preferred alkyl groups are those which are substituted by a group of the formula Vc, and amongst these, in particular, those having 1-4 C atoms.

As $C_2$-$C_{12}$ alkenyl, $R_{20}$, $R_{24}$ and $R_{27}$ are, for example, allyl, methallyl, n-hex-3-enyl, n-oct-4-enyl or n-undec-1-enyl. Alkenyl groups having 2-6 C atoms are preferred and these can be unsubstituted or substituted by a group of the formula Vc.

$R_{20}$ and $R_{27}$ can also be $C_5$-$C_{12}$ cycloalkyl. This is then, for example, cyclopentyl, cyclohexyl, methylcyclohexyl, cyclooctyl, dimethylcyclohexyl, propylcyclohexyl or dehydronaphthyl-α-methyl; especially cyclohexyl. If $R_{20}$ and $R_{27}$ are cycloalkyl, they are preferably substituted by a group of the formula Vc.

If $R_{20}$, $R_{24}$ and $R_{27}$ are $C_6$-$C_{14}$ aryl, this is intended to signify, for example, alkylphenyl having 1-8 C atoms, and especially having 1-4 C atoms, in the alkyl part, but especially phenyl. The aryl ring is preferably substituted by a group of the formula Vc.

Further preferred compounds are those in which one of $R_{20}$ and $R_{27}$ is hydrogen.

$R_{27}$ can preferably be a group of the formula VI.

As $C_1$-$C_8$ alkyl, $R_{21}$ is, for example, methyl, ethyl, iso-propyl, n-butyl, amyl, n-hexyl or n-octyl. Alkyl groups having 1-4 C atoms are preferred, but in particular $R_{21}$ is methyl or hydrogen.

As $C_1$-$C_{18}$ alkyl, $R_{23}$ an $R_{26}$ are, for example, methyl, ethyl, iso-propyl, n-butyl, t-butyl, amyl, n-hexyl, n-octyl, t-ocyl, n-decyl, n-dodecyl or n-octadecyl.

As $C_3$-$C_6$ alkenyl, $R_{23}$, $R_{25}$ and $R_{26}$ are, for example, allyl, methallyl, but-2-enyl or hex-3-enyl, especially allyl.

If $R_{23}$ and $R_{25}$ are $C_3$-$C_4$ alkynyl, this is especially propargyl.

As $C_5$-$C_7$ cycloalkyl, $R_{23}$, $R_{24}$ and $R_{25}$ are, for example, cyclopentyl, cyclohexyl or methylcyclohexyl, especially cyclohexyl.

As $C_6$-$C_{10}$ aryl, $R_{23}$ and $R_{25}$ are, for example, phenyl, α-naphthyl or β-naphthyl, especially phenyl.

If $R_{23}$ and $R_{25}$ are $C_7$-$C_{14}$ aralkyl, this is, for example, benzyl, α-phenylethyl or 2-phenylethyl, especially benzyl.

As $C_7$-$C_{14}$ alkylphenyl, $R_{23}$ is, for example 4-t-butylphenyl or 4-methylphenyl.

$R_{23}$ is, mreover, preferably also a group of the formula VI.

As $C_7$-$C_{14}$ aralkyl, $R_{24}$ is, for example, benzyl, α-phenylethyl or 2-phenylpropyl, especially benzyl. The aryl radical is preferably substituted by a group of the formula Vc.

As an aliphatic $C_1$-$C_{18}$ acyl radical, $R_{24}$ and $R_{26}$ are, for example, formyl, acetyl, propionyl, butyryl, octanoyl, dodecanoyl, stearoyl or acryloyl. As an aromatic $C_7$ acyl radical, $R_{24}$ and $R_{26}$ are benzoyl and as an araliphatic $C_8$-$C_9$ acyl radical $R_{24}$ and $R_{26}$ are cinnamoyl, phenylacetyl or phenylpropionyl. The aromatic part is unsubstituted or substituted by chlorine or $C_1$-$C_4$ alkyl, such as methyl, ethyl, n-propyl or t-butyl, or by $C_1$-$C_8$ alkoxy, such as methoxy, ethoxy, butoxy or octoxy, and/or hydroxyl. Substituted aromatic acyl groups are, for example, chlorobenzoyl, toluoyl, isopropylbenzoyl, 2,4-dichlorobenzoyl, 4-methoxybenzoyl, 3-butoxybenzoyl, 2-hydroxybenzoyl or 3,5-di-t.-butyl-4-hydroxybenzoyl. An araliphatic substituted acyl group is, for example, β-(3,5-di-t.-butyl-4-hydroxyphenyl)-propionyl. If $R_{24}$ and $R_{26}$ are alicyclic $C_6$-$C_9$ acyl groups, these can be cyclohexylcarbonyl or 2,4-dimethylcyclohexylcarbonyl.

A preferred meaning of $R_{25}$ is also a group —$CH_2$—$CH(R_5)$ —$OR_{16}$.

As $C_1$–$C_{12}$ alkylene, $R_{28}$ can be, for example, methylene, dimethylene, trimethylene, tetramethylene, hexamethylene, octamethylene, decamethylene or dodecamethylene.

As $C_6$–$C_{10}$ arylene, $R_{28}$ is, for example, phenylene or naphthylene.

Although compounds of the formula I which contain up to 4 groups of the formula Va, Vb or VI in the ligand L can certainly also be used industrially, those compounds containing 1 or 2 of the said groups are preferred for practical reasons. Further nitrogen heterocyclic compounds can, however, occur in the amine ligand A.

Amongst the groups Va, Vb and VI occurring in the molecule, those of the formula Va and VI are preferred in particular.

$X_1$ in formula Va is preferably

and $X_2$ in formula Vc is especially —O—.

As an anion having a single charge, B is, for example, an anion of an aliphatic or aromatic carboxylic acid, of a phosphonic acid half-ester, of a phosphinic acid, of a phosphinous acid or of an enol of the formula IX

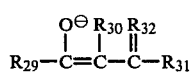

in which $R_{29}$ is alkyl, alkenyl, cycloalkyl, aralkyl or aryl and $R_{30}$ is hydrogen, alkyl, alkenyl, cycloalkyl, aralkyl, aryl or alkoxycarbonyl, or $R_{29}$ and $R_{30}$ together are subsituted or unsubsituted 1,4-butadi-1,3-enylene or 1,4-butylene, and $R_{31}$ is substituted or unsubsituted alkyl, alkenyl, cycloalkyl, aralkyl, aryl or alkoxy, or substituted or unsubstituted amino, and $R_{32}$ is oxo or substituted or unsubstituted imino.

An anion B, having a single charge, of an aliphatic carboxylic acid is especially an anion of a carboxylic acid $R_{33}$-COOH, in which $R_{33}$ is a substituted or unsubsituted aliphatic hydrocarbon radical, which is especially alkyl having 1–25, and in particular 1–12, C atoms, cycloalkyl having 5–12, and especially 5–6, C atoms, or alkenyl having 2–25, and especially 2–12, C atoms and in particular vinyl, these radicals being unsubstituted or substituted by halogen, especially chlorine, hydroxyl, alkyl having 1–6 C atoms or alkoxy having 1–6 C atoms.

Examples of $R_{33}$ are methyl, ethyl, n-hexyl, n-undecyl, 1-ethyl-n-pentyl, cyclopentyl, cyclohexyl, vinyl, allyl or crotonyl or 4-chlorobutyl.

An anion B, having a single charge, of an aliphatic carboxylic acid is also an anion of an aliphatic α- or β-aminocarboxylic acid, especially of such an acid having 2–20, and in particular 2–12 C atoms, which is unsubstituted on the amino group but preferably is monoalkylated or dialkylated on the amino group, such as by branched or, especially, straight-chain alkyl having 1–12 and in particular 1–8 C atoms. Examples of α-aminocarboxylic acids are glycine, α-alanine, valine and isoleucine, which are monosubstituted or disubstituted on the amino group, especially by n-alkyl having 1–8 C atoms, such as di-n-octyl-glycine. An example of β-aminoccarboxylic acids is β-alanine which is monosubstituted or disubstituted on the amino group, especially by n-alkyl having 1–8 C atoms, such as di-n-propyl-β-alanine.

An anion B, having a single charge, of an aromatic carboxylic acid is especially an anion of a carboxylic acid $R_{34}$-COOH, in which $R_{34}$ is a substituted or unsubstituted aromatic hydrocarbon radical, which is especially aryl having 6–10 C atoms or aralkyl having 7–14 C atoms. The radical can be, in particular, phenyl, benzyl or phenylethyl and these can be unsubstituted in the aryl part. Substituents in the aryl part are, especially, hydroxyl, cyclohexyl, phenyl, benzyl, α, α-dimethylbenzyl and especially $C_1$–$C_{12}$ alkyl, such as methyl, ethyl, iso-propyl, t.-butyl, t-octyl or n-dodecyl, especially t-butyl. Therefore, $R_{34}$ can be, for example, 3,5-di-t.-butyl-4-hydroxyphenyl-ethyl, 3,5-di-t.-butyl-4-hydroxybenzyl or 3,5-di-t.-butyl-4-hydroxybenzyl or 3,5-di-t.-butyl-4-hydroxyophenyl.

An anion B, having a single charge, of a phosphonic acid half-ester or of a phosphinic acid is, especially, an anion of a phosphonic acid half-ester or of a phosphinic acid of the formulae X, XI or XII

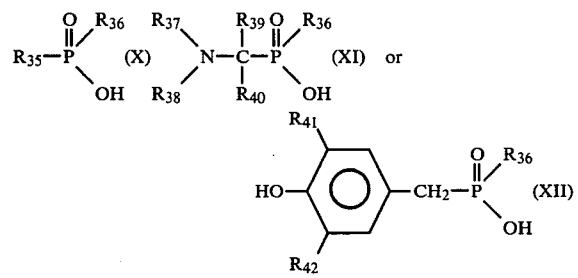

in which $R_{35}$ is $C_1$–$C_{18}$ alkyl and $R_{36}$ is $C_1$–$C_8$ alkyl, cyclohexyl, or $C_7$–$C_{11}$ aralkyl or phenyl which are unsubstituted or monosubstituted by chlorine, $C_1$–$C_4$ alkyl or methoxy, or $C_1$–$C_4$ alkoxy, benzyloxy, phenoxy or tolyloxy and $R_{37}$ and $R_{38}$ independently of one another are hydrogen, $C_1$–$C_8$ alkyl, cyclohexyl, or $C_7$–$C_{11}$ aralkyl or phenyl which are unsubstituted or monosubstituted or disubstituted by chlorine, $C_1$–$C_4$ alkyl and/or $C_1$–$C_4$ alkoxy, or $R_{37}$ and $R_{38}$ together with the N atom to which they are bonded form a pyrrolidine, piperidine or morpholine ring, and $R_{39}$ is hydrogen, $C_1$–$C_6$ alkyl, phenyl or 4-methoxyphenyl and $R_{40}$ is hydrogen or methyl and $R_{41}$ and $R_{42}$ independently of one another are $C_1$–$C_{12}$ alkyl.

As $C_1$–$C_{18}$ alkyl, $R_{35}$ is, for example, methyl, ethyl, propyl, n-butyl, n-hexyl, n-octyl, n-dodecyl, or n-octadecyl, and especially $C_1$–$C_4$ alkyl.

As $C_1$–$C_8$ alkyl, $R_{36}$, $R_{37}$ and $R_{38}$ are, for example, linear or branched alkyl groups, such as methyl, ethyl, propyl, isopropyl, n-butyl, n-hexyl, n-octyl or 2-ethylhexyl; $C_1$–$C_4$ alkyl groups are preferred.

As $C_7$–$C_{11}$ aralkyl, which can be substituted or unsubstituted, $R_{36}$, $R_{37}$ and $R_{38}$ are, for example, benzyl, 4-methylbenzyl, 4-isopropylbenzyl, 3-chlorobenzyl, 4-methoxybenzyl or phenylethyl, especially benzyl.

As phenyl, which can be substituted or unsubstituted, $R_{36}$, $R_{37}$ and $R_{38}$ are, for example, phenyl, 4-methylphenyl, 3-chlorophenyl, 4-methoxyphenyl or 4-butoxyphenyl, especially phenyl.

As $C_1$–$C_4$ alkoxy, $R_{36}$ is, for example, methoxy, ethoxy, propoxy or butoxy.

$R_{37}$ and $R_{38}$, together with the nitrogen atom to which they are bonded, can also form a pyrrolidine, piperidine or morpholine ring, especially a piperidine or morpholine ring.

As $C_1-C_6$ alkyl, $R_{39}$ is, for example, methyl, ethyl, propyl, n-butyl or n-hexyl, especially methyl.

A further preferred meaning of $R_{39}$ is hydrogen.

As $C_1-C_{12}$ alkyl, $R_{41}$ and $R_{42}$ independently of one another are, for example, methyl, ethyl, ispropyl, t-butyl, amyl, hexyl, t-octyl or n-dodecyl. Alkyl groups having 1-4 C atoms, especially t-butyl, are preferred.

An anion B, having a single charge, of a phosphinous acid is especially an anion of a phosphinous acid of the formula

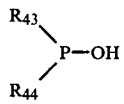 (XIII)

in which $R_{43}$ and $R_{44}$ independently of one another are alkyl, or phenyl, benzyl or cyclohexyl which are unsubstituted or substituted by chlorine, alkyl and/or alkoxy.

If $R_{43}$ and $R_{44}$ independently of one another are alkyl, this is especially alkyl having 1-18 C atoms, such as methyl, ethyl, n-butyl, n-hexyl, n-octyl, n-dodecyl or n-octadecyl.

If $R_{43}$ and $R_{44}$ independently of one another are phenyl, benzyl or cyclohexyl, these can be unsubstituted or monosubstituted or disubstituted by chlorine, $C_1-C_4$ alkyl and/or $C_1-C_4$ alkoxy. Possible radicals are 4-methoxyphenyl, 3-chlorobenzyl, 4-butylphenyl, 4-methylcyclohexyl or 3-chloro-4-methylphenyl.

If B, as an anion having a single charge, is an enol of the formula IX, $R_{29}$, $R_{30}$ and $R_{31}$, as alkyl, are especially alkyl having 1-12 C atoms and in particular having 1-6 C atoms, such as methyl, ethyl, n-propyl, n-butyl or n-hexyl.

As alkenyl, $R_{29}$, $R_{30}$ and $R_{31}$ are especially alkenyl having 2-12 C atoms and in particular 2-6 C atoms, such as allyl, methallyl or n-hex-3-enyl.

As cycloalkyl, $R_{29}$, $R_{30}$ and $R_{31}$ are especially cycloalkyl having 5-12 and in particular 5-6 C atoms, such as cyclohexyl.

As aralkyl, $R_{29}$, $R_{30}$ and $R_{31}$ are especially aralkyl having 7-12 C atoms, such as benzyl or phenylethyl.

As aryl, $R_{29}$, $R_{30}$ and $R_{31}$ are especially aryl having 6-10 C atoms, such as phenyl, naphthyl or phenyl substituted by alkyl having 1-12 and especially 1-4 C atoms, such as methyl, ethyl or butyl; by alkoxy having 1-12 and especially 1-4 C atoms, such as methoxy or butoxy, or by halogen, such as chlorine.

As alkoxycarbonyl, $R_{30}$ is especially alkoxycarbonyl having 2-12 and in particular 2-6 C atoms, such as methoxycarbonyl or ethoxycarbonyl.

Substituted or unsubstituted 1,4-butadi-1,3-enylene as $R_{29}$ and $R_{30}$ is especially unsubstituted 1,4-butadi-1,3-enylene, or 1,4-butadi-1,3-enylene which carries as a substituent, for example, $C_1-C_{12}$ alkyl, especially $C_1-C_6$ alkyl, such as methyl; $C_1-C_{12}$ alkoxy, especially $C_1-C_4$ alkoxy, such as n-butoxy; or halogen, such as chlorine.

As substituted alkyl, $R_{31}$ is especially alkyl having 1-12 and in particular 1-6 C atoms which carries halogen, such as chlorine, as substituents.

If $R_{31}$ is alkoxy, it is especially alkoxy having 1-12, and in particular 1-6, C atoms, such as methoxy or ethoxy.

$R_{31}$ can be an amino group; if this is substituted it is especially alkylamino having 1-12 C atoms, such as methylamino, dialkylamino having 2-24 C atoms, such as dimethylamino, and especially anilino, the phenyl ring of which is unsubstituted or carries alkyl having 1-6 C atoms, such as methyl, or especially alkoxy having 1-6 C atoms, such as methoxy, as substituents in the p-position, m-position or, especially, o-position.

Preferred anions B having a single charge are, in particular, those of an aliphatic or aromatic carboxylic acid, of a phosphonic acid or of an enol of the formula IX.

s is 0 to 2 and is preferably 0.

Preferred metal complexes are those of the formula XIV

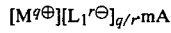 (XIV)

in which M is $Mg^{2+}$, $VO^{2+}$, $Ca^{2+}$, $Mn^{2+}$, $Zn^{2+}$, $Co^{2+}$, $Ni^{2+}$ or $Al^{3+}$ and q is 2 or 3 and $L_1$ is a t-dentate group of the formula IVa which is substituted by at least one group of the formulae Va, Vb or VI, and u is 0, 1 or 2 and t is 3, and $R_{15}$ and $R_{16}$ independently of one another are hydrogen or $C_1-C_{18}$ alkyl which can be unsubstituted or substituted by a group of the formulae Va, Vb or Vc; or a group Vc, or a group of the formula VI in the p-position, halogen or a radical —$OR_{24}$, or $R_{15}$ and $R_{16}$ together form a 1,3-butadiene-1,4-diyl radical, and $R_5$ is hydrogen, methyl or phenyl and Y is hydrogen, oxyl, $C_1-C_{12}$ alkyl, $C_3-C_{12}$ alkenyl, $C_3-C_6$ alkynyl, $C_2-C_{21}$ alkoxyalkyl, $C_7-C_9$ aralkyl, 2,3-epoxypropyl, an aliphatic $C_1-C_4$ acyl group or one of the groups —$CH_2COOR_6$, —$CH_2$—$CH(R_7)$—$OR_8$, —$COOR_9$ or —$CONHR_9$, in which $R_6$ is $C_1-C_{12}$ alkyl, $C_3-C_6$ alkenyl, phenyl, $C_7-C_8$ aralkyl or cyclohexyl and $R_7$ is hydrogen, methyl or phenyl and $R_8$ is hydrogen, an aliphatic $C_1-C_{18}$ acyl group or an aromatic $C_7$ acyl group, an araliphatic $C_8-C_9$ acyl group or an alicyclic $C_6-C_9$ acyl group, in which the aromatic part can be unsubstituted or substituted by chlorine, $C_1-C_4$ alkyl, $C_1-C_8$ alkoxy and/or hydroxyl, and $R_9$ is $C_1-C_{12}$ alkyl, cyclohexyl, phenyl or benzyl, and $X_1$ and $X_2$ independently of one another are —O— or

and $R_{21}$ is hydrogen or $C_1-C_8$ alkyl and $R_{22}$ is hydrogen or a group —$X_1R_{26}$ and Z is —O— or

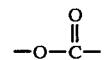

and $R_{23}$ is $C_1-C_{18}$ alkyl, $C_3-C_6$ alkenyl, $C_3-C_4$ alkynyl, $C_5-C_7$ cycloalkyl, $C_6-C_{10}$ aryl, $C_7-C_{14}$ aralkyl, $C_7-C_{14}$ alkylphenyl or a group of the formula VI, in which Y and $R_{21}$ are as defined, and $R_{24}$ is hydrogen or $C_1-C_8$ alkyl, $C_5-C_7$ cycloalkyl, $C_6-C_{14}$ aryl, $C_7-C_{14}$ aralkyl or $C_2-C_{12}$ alkenyl which are unsubstituted or substituted by a group of the formula Vc, in which $X_2$ and $R_{23}$ are as defined, or is an aliphatic $C_1-C_{18}$ acyl group, aromatic $C_7$ acyl group, araliphatic $C_8-C_9$ acyl group or alicyclic $C_6-C_9$ acyl group which is unsubstituted or substituted by chlorine, $C_1-C_8$ alkyl, $C_1-C_8$ alkoxy, a group Vc and/or hydroxyl, and $R_{25}$ is hydrogen, $C_1-C_{18}$ alkyl, which can be unsubstituted or substituted by a group of the formula Vc, in which $X_2$ and $R_{23}$ are as defined, or $C_3-C_6$ alkenyl, $C_3-C_4$ alkynyl, $C_5-C_7$ cycloalkyl, $C_6-C_{10}$ aryl, $C_7-C_{14}$ aralkyl, a group of the formula $CH_2-CH(R_5)-OR_{26}$ or a group of the formula VI, and $R_{26}$ is hydrogen, $C_1-C_{18}$ alkyl, $C_3-C_6$ alkenyl, cyclohexyl, benzyl or an aliphatic $C_1-C_{18}$ acyl group, aromatic $C_7$ acyl group, araliphatic $C_8-C_9$ acyl group or alicyclic $C_6-C_9$ acyl group which is unsubstituted or substituted by chlorine, $C_1-C_8$ alkyl, $C_1-C_8$ alkoxy and/or hydroxyl, and r is 1 or 2 and m is a number from 0 to 3, the sum $(3 \cdot q/r)+m$ being equal to the coordination number of the metal ion M, and A is $H_2O$ or an amine of the formula III, in which $R_{12}$ is unsubstituted or $-OH-$ substituted $C_1-C_{18}$ alkyl, $C_5-C_{12}$ cycloalkyl, $C_6-C_{18}$ aryl, $C_7-C_{20}$ aralkyl, a substituted or unsubstituted aminoalkyl group or a piperidinyl group, and $R_{13}$ is hydrogen or unsubstituted or $-OH$-substituted $C_1-C_{18}$ alkyl, $C_5-C_{12}$ cycloalkyl, a substituted or unsubstituted aminoalkyl group or a piperidinyl group, or $R_{12}$ and $R_{13}$ together with the N atom form a pyrrolidine, piperidine or morpholine ring which is substituted by alkyl groups or is unsubstituted, and $R_{14}$ is hydrogen or unsubstituted or $-OH$-substituted $C_1-C_{18}$ alkyl.

Amongst the compounds of the formula XIV, those to be mentioned in particular are those in which M is $Ca^{2+}$, $Mn^{2+}$, $Zn^{2+}$, $Co^{2+}$, $Ni^{2+}$ or $Al^{3+}$ and q is 2 or 3 and u is 0 and $L_1$ and t are as defined above, and $R_{15}$ and $R_{16}$ independently of one another are hydrogen or $C_1-C_8$ alkyl which can be unsubstituted or substituted by a group of the formulae Va, Vb or Vc; or a group Vc or a radical $-OR_{24}$, and $R_5$ is hydrogen or methyl and Y is hydrogen, $C_1-C_4$ alkyl, $C_3-C_6$ alkenyl, propargyl, $C_2-C_5$ alkoxyalkyl, benzyl, acetyl or one of the groups $-CH_2COOR_6$, $-CH_2CH(R_7)-OR_8$, $-COOR_9$ or $-CONHR_9$, in which $R_6$ is $C_1-C_4$ alkyl and $R_7$ is hydrogen or methyl and $R_8$ is hydrogen and $R_9$ is $C_1-C_4$ alkyl, and $X_1$ and $X_2$ independently of one another are $-O-$ or

and $R_{21}$ is hydrogen or $C_1-C_4$ alkyl and $R_{22}$ and Z are as defined above, and $R_{23}$ is $C_1-C_{18}$ alkyl, allyl, propargyl, cyclohexyl, phenyl, 4-t-butylphenyl or a group of the formula VI, in which Y and $R_{21}$ are as defined, and $R_{24}$ is hydrogen or $C_1-C_{12}$ alkyl, $C_2-C_6$ alkenyl, cyclohexyl, phenyl or benzyl which are unsubstituted or substituted by a group of the formula Vc, in which $X_2$ and $R_{23}$ are as defined, and $R_{25}$ is hydrogen, $C_1-C_{12}$ alkyl, which can be unsubstituted or substituted by a group of the formula Vc, in which $X_2$ and $R_{23}$ are as defined, or allyl, propargyl, cyclohexyl, phenyl, benzyl or a group $-CH_2-CH(R_5)-OH$, in which $R_5$ is as defined, and r and m and also the sum $(3 \cdot q/r)+m$ are as defined above, and A is $H_2O$ or an amine of the formula III, in which $R_{12}$ and $R_{13}$ independently of one another are $C_1-C_8$ alkyl, $C_1-C_6$ hydroxyalkyl or a substituted aminoalkyl group of the formula IId

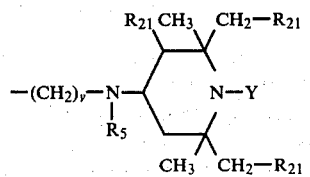

in which v is 1 to 8 and Y, $R_5$ and $R_{21}$ are as defined, or $R_{12}$ and $R_{13}$ together form a piperidine group, and $R_{14}$ is hydrogen or $C_1-C_8$ alkyl or $C_1-C_6$ hydroxyalkyl.

Particularly preferred compounds of the formula XIV are those in which M is $Ca^{2+}$, $Zn^{2+}$ or $Ni^{2+}$ and q is 2 and u is 0 and $L_1$ is a t-dentate group of the formula IVa, which is substituted by at least one group of the formulae Va or VI, and t is 2, and $R_{15}$ is $-OR_{24}$, $C_1-C_4$ alkyl substituted by a group Va or Vc, or a group Vc and $R_{16}$ is hydrogen or $C_1-C_8$ alkyl, and $R_5$ is hydrogen or methyl and Y is hydrogen, methyl or acetyl and $X_1$ is

and $X_2$ is $-O-$ and $R_{21}$ is hydrogen or methyl and $R_{23}$ is a group of the formula VI, and $R_{24}$ is $C_1-C_4$ alkyl substituted by a group of the formula Vc, in which $X_2$ and $R_{23}$ are as defined, and $R_{25}$ is hydrogen, $C_1-C_{12}$ alkyl, cyclohexyl, benzyl, phenyl or a group of the formula $-CH_2-CH(R_5)-OH$, and r is 1 and m is 0.

Compounds of very particular interest are those of the formula XIV in which $R_{15}$ is a $C_1-C_4$ alkyl group which is substituted by a group of the formula Va and is in the o-position and $R_{16}$ is a 1,1,3,3-tetramethylbutyl group in the p-position.

Examples of compounds of the formula XIV are: the 1:2 $Ni^{2+}$ complex of di-{2-hydroxy-5-t-octyl-3-[N-methyl-N-(2,2,6,6-tetramethyl-piperidin-4-yl)-aminomethyl]-phenyl} sulphide, the 1:2 $Ni^{2+}$ or $Ca^{2+}$ complex of di-{2-hydroxy-5-t-octyl-3-[1,2,2,6,6-pentamethyl-piperidin-4-oxycarbonylmethyl]-phenyl} sulphide, the 1:1 $Zn^{2+}$ complex of di-{2-hydroxy-5-[1,2,2,6,6-pentamethyl-piperidin-4-yl]-phenyl} sulphide.(4-amino-1,2,2,6,6-pentamethylpiperidine)$_3$, the 1:2 $Ni^{2+}$ complex of di-{2-hydroxy-5-[2,2,6,6-tetramethylpiperidin-4-yl]-phenyl} sulphide, the 1:1 $Ca^{2+}$ or $Ni^{2+}$ complex of di-{2-hydroxy-5-t-octyl-3-[2,2,6,6-tetramethyl-piperidin-4-oxy-carbonyl-methyl]-phenyl} sulphide.(4-amino-2,2,6,6-tetramethyl-piperidine)$_3$ and the 1:1 $Ni^{2+}$ complex of di-{2-hydroxy-5-t-octyl-3-[N-(2,3,6-trimethyl-2,6-diethyl-piperidin-4-yl)-amino]-phenyl} sulphide.(triethanolamine)$_3$.

Further preferred metal complexes are those of the formula XV $$[M^{q\oplus}] [L_2{}^{r\ominus}]_{q/r} \cdot mA \qquad (XV)$$

in which M is $Mg^{2+}$, $VO^{2+}$, $Ca^{2+}$, $Mn^{2+}$, $Zn^{2+}$, $Co^{2+}$, $Ni^{2+}$ or $Al^{3+}$ and q is 2 or 3 and $L_2$ is a t-dentate group of the formula IVb, which is substituted by at least one group of the formulae Va, Vb or VI, and t is 2, and $R_{15}$ and $R_{16}$ independently of one another are hydrogen, $C_1-C_{18}$ alkyl, which can be unsubstituted or substituted by a group of the formulae Va, Vb or Vc, or a group Vc, or a group of the formula VI in the p-position, halogen or a radical of the formula $-OR_{24}$, or $R_{15}$ and $R_{16}$ together form a 1,3-butadiene-1,4-diyl radical, and $R_5$ is hydrogen, methyl or phenyl and Y is hydrogen, oxyl, $C_1-C_{12}$ alkyl, $C_3-C_{12}$ alkenyl, $C_3-C_6$ alkynyl, $C_2-C_{21}$ alkoxyalkyl, $C_7-C_9$ aralkyl, 2,3-epoxypropyl, an aliphatic $C_1-C_4$ acyl group or one of the groups $-CH_2COOR_6$, $-CH_2-CH(R_7)-OR_8$, $-COOR_9$ or $-CONHR_9$, in which $R_6$ is $C_1-C_{12}$ alkyl, $C_3-C_6$ alkenyl, phenyl, $C_7-C_8$ aralkyl or cyclohexyl and $R_7$ is hydrogen, methyl or phenyl and $R_8$ is hydrogen, an aliphatic $C_1$-$C_{18}$ acyl group or an aromatic $C_7$ acyl group, an araliphatic $C_8$-$C_9$ acyl group or an alicyclic $C_6$-$C_9$ acyl group, in which the aromatic part can be unsubstituted or substituted by chlorine, $C_1$-$C_4$ alkyl, $C_1$-$C_8$ alkoxy and/or hydroxyl, and $R_9$ is $C_1$-$C_{12}$ alkyl, cyclohexyl, phenyl or benzyl, and $X_1$ and $X_2$ independently of one another are —O— or

and $R_{21}$ is hydrogen or $C_1$-$C_8$ alkyl and $R_{22}$ is hydrogen or a group —$X_1R_{26}$, and Z is —O— or

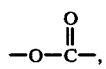

and $R_{23}$ is $C_1$-$C_{18}$ alkyl, $C_3$-$C_6$ alkenyl, $C_3$-$C_4$ alkynyl, $C_5$-$C_7$ cycloalkyl, $C_6$-$C_{10}$ aryl, $C_7$-$C_{14}$ aralkyl, $C_7$-$C_{14}$ alkylphenyl or a group of the formula VI, in which Y and $R_{21}$ are as defined, and $R_{24}$ is hydrogen or $C_1$-$C_8$ alkyl, $C_5$-$C_7$ cycloalkyl, $C_6$-$C_{14}$ aryl, $C_7$-$C_{14}$ aralkyl or $C_2$-$C_{12}$ alkenyl which are unsubstituted or substituted by a group of the formula Vc, in which $X_2$ and $R_{23}$ are as defined; or an aliphatic $C_1$-$C_{18}$ acyl group, aromatic $C_7$ acyl group, araliphatic $C_8$-$C_9$ acyl group or alicyclic $C_6$-$C_9$ acyl group, which is unsubstituted or substituted by chlorine, $C_1$-$C_8$ alkyl, $C_1$-$C_8$ alkoxy, a group Vc and/or hydroxyl, and $R_{25}$ is hydrogen, $C_1$-$C_{18}$ alkyl, which can be unsubstituted or substituted by a group of the formula Vc, in which $X_2$ and $R_{23}$ are as defined, or $C_3$-$C_6$ alkenyl, $C_3$-$C_4$ alkynyl, $C_5$-$C_7$ cycloalkyl, $C_6$-$C_{10}$ aryl, $C_7$-$C_{14}$ aralkyl, a group of the formula $CH_2$—$CH(R_5)$—$OR_{26}$ or a group of the formula VI and $R_{26}$ is hydrogen, $C_1$-$C_{18}$ alkyl, $C_3$-$C_6$ alkenyl, cyclohexyl, benzyl or an aliphatic $C_1$-$C_{18}$ acyl group, aromatic $C_7$ acyl group, araliphatic $C_8$-$C_9$ acyl group or alicyclic $C_6$-$C_9$ acyl group, which is unsubstituted or substituted by chlorine, $C_1$-$C_8$ alkyl, $C_1$-$C_8$ alkoxy and/or hydroxyl, and $R_{17}$ is hydrogen, $C_1$-$C_{18}$ alkyl, halogen, a group —$OR_{24}$, or a group of the formula Vc in which $R_{23}$, $R_{24}$ and $X_2$ are as defined, and r is 1 and m is an integer from 0 to 2, the sum (2.q)+m being equal to the coordination number of the metal ion M, and A is $H_2O$ or an amine of the formula III, in which $R_{12}$ is unsubstituted or —OH-substituted $C_1$-$C_{18}$ alkyl, $C_5$-$C_{12}$ cycloalkyl, $C_6$-$C_{18}$ aryl, $C_7$-$C_{20}$ aralkyl, a substituted or unsubstituted aminoalkyl group or a piperidinyl group and $R_{13}$ is hydrogen or unsubstituted or —OH-substituted $C_1$-$C_{18}$ alkyl, $C_5$-$C_{12}$ cycloalkyl, a substituted or unsubstituted aminoalkyl group or a piperidinyl group, or $R_{12}$ and $R_{13}$ together with the N atom form a pyrrolidine, piperidine or morpholine ring which is substituted by alkyl groups or is unsubstituted, and $R_{14}$ is hydrogen or unsubstituted or —OH-substituted $C_1$-$C_{18}$ alkyl.

Amongst the compounds of the formula XV, those to be mentioned in particular are those in which M is $Ca^{2+}$, $Mn^{2+}$, $Zn^{2+}$, $Co^{2+}$, $Ni^{2+}$ or $Al^{3+}$ and q is 2 or 3 and $L_2$ and t are as defined above, and $R_{15}$ and $R_{16}$ independently of one another are hydrogen or $C_1$-$C_8$ alkyl, which can be unsubstituted or substituted by a group of the formulae Va, Vb or Vc; or a group Vc or a radical —$OR_{24}$, and $R_5$ is hydrogen or methyl and Y is hydrogen, $C_1$-$C_4$ alkyl, $C_3$-$C_6$ alkenyl, propargyl, $C_2$-$C_5$ alkoxyalkyl, benzyl, acetyl or one of the groups —$CH_2COOR_6$, —$CH_2CH(R_7)$—$OR_8$, —$COOR_9$ or —$CONHR_9$, in which $R_6$ is $C_1$-$C_4$ alkyl and $R_7$ is hydrogen or methyl and $R_8$ is hydrogen and $R_9$ is $C_1$-$C_4$ alkyl, and $X_1$ and $X_2$ independently of one another are —O— or

and $R_{21}$ is hydrogen or $C_1$-$C_4$ alkyl and $R_{22}$ and Z are as defined above, and $R_{23}$ is $C_1$-$C_{18}$ alkyl, allyl, propargyl, cyclohexyl, phenyl, 4-t-butylphenyl or a group of the formula VI, in which Y and $R_{21}$ are as defined, and $R_{24}$ is hydrogen or $C_1$-$C_{12}$ alkyl, $C_2$-$C_6$ alkenyl, cyclohexyl, phenyl or benzyl, which are unsubstituted or substituted by a group of the formula Vc, in which $X_2$ and $R_{23}$ are as defined, and $R_{25}$ is hydrogen, $C_1$-$C_{12}$ alkyl, which can be unsubstituted or substituted by a group of the formula Vc, in which $X_2$ and $R_{23}$ are as defined, or allyl, propargyl, cyclohexyl, phenyl, benzyl or a group —$CH_2$—$CH(R_5)$—OH, in which $R_5$ is as defined, and $R_{17}$ is hydrogen, $C_1$-$c_{12}$ alkyl, a radical —$OR_{24}$ or a group of the formula Vc, in which $R_{23}$, $R_{24}$ and $X_2$ are as defined, and r and m and also the sum (2.q)+m are as defined above, and A is $H_2O$ or an amine of the formula III, in which $R_{12}$ and $R_{13}$ independently of one another are $C_1$-$C_8$ alkyl, $C_1$-$C_6$ hydroxyalkyl or a substituted aminoalkyl group of the formula IId

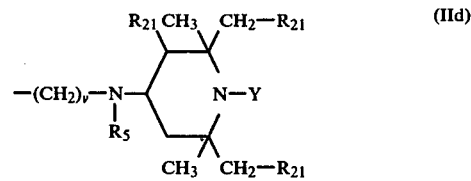

in which v is 1 to 8 and Y, $R_5$ and $R_{21}$ are as defined, or $R_{12}$ and $R_{13}$ together form a piperidine group, and $R_{14}$ is hydrogen or $C_1$-$C_8$ alkyl or $C_1$-$C_6$ hydroxyalkyl.

Particularly preferred compounds of the formula XV are those in which M is $Ca^{2+}$, $Zn^{2+}$ or $Ni^{2+}$ and q is 2 and $L_2$ is a t-dentate group of the formula IVb, which is substituted by at least one group of the formulae Va or VI, and t is 2, and $R_{15}$ is hydrogen, $C_1$-$C_5$ alkyl, a radical —$OR_{24}$, $C_1$-$C_4$ alkyl substituted by a group Va or Vc, or a group Vc and $R_{16}$ is hydrogen or $C_1$-$C_8$ alkyl and $R_{17}$ is hydrogen, and $R_5$ is hydrogen or methyl and Y is hydrogen, methyl or acetyl and $X_1$ is

and $X_2$ is —O— and $R_{21}$ is hydrogen or methyl and $R_{23}$ is a group of the formula VI, and $R_{24}$ is $C_1$-$C_4$ alkyl substituted by a group of the formula Vc, in which $X_2$ and $R_{23}$ are as defined, and $R_{25}$ is hydrogen, $C_1$-$C_{12}$ alkyl, cyclohexyl, benzyl or —$CH_2$—$CH(R_5)$—OH, and r, m, the sum (2.q)+m, A, $R_{12}$, $R_{13}$ and $R_{14}$ are as defined.

Compounds of very particular interest are those of the formula XV in which $R_{15}$ is a $C_1$-$C_4$ alkyl group which is in the o-position relative to the hydroxyl group and is substituted by a group of the formula Va, or especially also a group of the formula —$OR_{24}$ which is in the m-position relative to the hydroxyl group and in which $R_{24}$ is a $C_1-C_4$ alkyl group substituted by a group of the formula Vc, and $R_{16}$ and $R_{17}$ are hydrogen.

Examples of compounds of the formula XV are: the 1:2 $Ni^{2+}$ complex of 2-(2'-hydroxy-5'-t-butylphenyl)-5-(N-benzyl-2,2,6,6-tetramethyl-piperidin-4-oxycarbonyl)-benztriazole. ((triethanomaine)$_2$, the 1:2 $Ca^{2+}$ complex of 2-{2'-hydroxy-5'-t-butyl-4'-[2*-di-(1,2,2,6,6-pentamethyl-piperidin-4-oxycarbonyl)-hexyl]-phenyl}-benztriazole. (4-amino-2,2,6,6-tetramethyl-piperidine)$_2$, the 1:2 $Zn^{2+}$ complex of 2-{2'-hydroxy-5'-sec-butyl)-4'-[2*-di-(1-acetyl-2,2,6,6-tetramethyl-piperidin-4-oxy-carbonyl)-hexyl]-phenyl}-4-(1-acetyl-2,2,6,6-tetramethyl-piperidin-4-oxycarbonyl)-benztriazole. (4-dimethylamino-2,2,6,6-tetramethyl-piperidine)$_2$ and the 1:2 $Ni^{2+}$ complex of 2-{2'-hydroxy-3'-sec-butyl)-4'-[1,2,2,6,6-pentamethyl-piperidin-4-oxycarbonyl]-phenyl}-benzriazole. (N,N'-methyl-N,N'-(1,2,2,6,6-pentamethyl-piperidin-4-yl)-ethylenediamine.

Further preferred metal complexes are those of the formula XVI $$[M^{q\oplus}][L_3{}^{r\ominus}]_{q/r}mA \qquad (XVI)$$

in which M is $Mg^{2+}$, $VO^{2+}$, $Ca^{2+}$, $Mn^{2+}$, $Zn^{2+}$, $Co^{2+}$, $Ni^{2+}$ or $Al^{3+}$ and q is 2 or 3 and $L_3$ is a t-dentate group of the formula IVc, which is substituted by at least one group of the formulae Va, Vb or VI, and t is 2 or 4, and $R_{15}$ and $R_{16}$ indepdendently of one another are hydrogen or $C_1-C_{18}$ alkyl, which can be unsubstituted or substituted by a group of the formulae Va, Vb or Vc; or a group Vc, a group of the formula VI in the p-position, halogen or a radical $-OR_{24}$, or $R_{15}$ and $R_{16}$ together form a 1,3-butadiene-1,4-diyl radical, and $R_5$ is hydrogen, methyl or phenyl and Y is hydrogen, oxyl, $C_1-C_{12}$ alkyl, $C_3-C_{12}$ alkenyl, $C_3-C_6$ alkynyl, $C_2-C_{21}$ alkoxyalkyl, $C_7-C_9$ aralkyl, 2,3-epoxypropyl, an aliphatic $C_1-C_4$ acyl group or one of the groups $-CH_2COOR_6$, $-CH_2-CH(R_7)-OR_8$, $-COOR_9$ or $-CONHR_9$, in which $R_6$ is $C_1-C_{12}$ alkyl, $C_3-C_6$ alkenyl, phenyl, $C_7-C_8$ aralkyl or cyclohexyl and $R_7$ is hydrogen, methyl or phenyl and $R_8$ is hydrogen, an aliphatic $C_1-C_{18}$ acyl group or an aromatic $C_7$ acyl group, an araliphatic $C_8-C_9$ acyl group or an alicyclic $C_6-C_9$ acyl group, in which the aromatic part can be unsubstituted or substituted by chlorine, $C_1-C_4$ alkyl, $C_1-C_8$ alkoxy and/or hydroxyl, and $R_9$ is $C_1-C_{12}$ alkyl, cyclohexyl, phenyl or benzyl, and $X_1$ and $X_2$ independently of one another are $-O-$ or

and $R_{21}$ is hydrogen or $C_1-C_8$ alkyl and $R_{22}$ is hydrogen or a group $-X_1R_{26}$ and Z is $-O-$ or

and $R_{23}$ is $C_1-C_{18}$ alkyl, $C_3-C_6$ alkenyl, $C_3-C_4$ alkynyl, $C_5-C_7$ cycloalkyl, $C_6-C_{10}$ aryl, $C_7-C_{14}$ aralkyl, $C_7-C_{14}$ alkylphenyl or a group of the formula VI, in which Y and $R_{21}$ are as defined, and $R_{24}$ is hydrogen or $C_1-C_8$ alkyl, $C_5-C_7$ cycloalkyl, $C_6-C_{14}$ aryl, $C_7-C_{14}$ aralkyl or $C_2-C_{12}$ alkenyl, which are unsubstituted or substituted by a group of the formula Vc, in which $X_2$ and $R_{23}$ are as defined; or an aliphatic $C_1-C_{18}$ acyl group, aromatic $C_7$ acyl group, araliphatic $C_8-C_9$ acyl group or alicyclic $C_6-C_9$ acyl group, which is unsubstituted or substituted by chlorine, $C_1-C_8$ alkyl, $C_1-C_8$ alkoxy, a group Vc and/or hydroxyl, and $R_{25}$ is hydrogen, $C_1-C_{18}$ alkyl, which can be unsubstituted or substituted by a group of the formula Vc, in which $X_2$ and $R_{23}$ are as defined, or $C_3-C_6$ alkenyl, $C_3-C_4$ alkynyl, $C_5-C_7$ cycloalkyl, $C_6-C_{10}$ aryl, $C_6-C_{14}$ aralkyl, a group of the formula $CH_2-CH(R_5)-OR_{26}$ or a group of the formula VI, and $R_{26}$ is hydrogen, $C_1-C_{18}$ alkyl, $C_3-C_6$ alkenyl, cyclohexyl, benzyl or an aliphatic $C_1-C_{18}$ acyl group, aromatic $C_7$ acyl group, araliphatic $C_8-C_9$ acyl group or alicyclic $C_6-C_9$ acyl group, which is unsubstituted or substituted by chlorine, $C_1-C_8$ alkyl, $C_1-C_8$ alkoxy and/or hydroxyl, and $R_{18}$ is a group $-N(R_{25})R_{27}$ and $R_{19}$ is hydrogen, or $R_{18}$ and $R_{19}$ together are $=O$ or $=NR_{27}$, and $R_{20}$ is hydrogen, $C_7-C_{14}$ aralkyl, $C_7-C_{14}$ alkylphenyl or $C_1-C_{18}$ alkyl, $C_2-C_{12}$ alkenyl, $C_5-C_{12}$ cycloalkyl or $C_6-C_{14}$ aryl, which are unsubstituted or substituted by a group of the formula Vc, or a group of the formula VII or, if $R_{18}$ and $R_{19}$ together are $=O$, a group of the formula Va; in which $X_1$, $R_{21}$ and Y are as defined above, and $R_{28}$ is $C_1-C_{12}$ alkylene, butenylene, $C_6-C_{10}$ arylene or diphenylene, and $R_{27}$ is hydrogen, $C_7-C_{14}$ aralkyl, $C_7-C_{14}$ alkylphenyl, a group $-OR_{24}$, or $C_1-C_{18}$ alkyl, $C_2-C_{12}$ alkenyl, $C_5-C_{12}$ cylcoalkyl or $C_6-C_{14}$ aryl which are unsubstituted or substituted by a group of the formula Vc, or a group of the formula VI or a group of the formula $-CH_2-CH(R_5)-OR_{26}$; or, if $R_{20}$ is not a group of the formula VII, $R_{27}$ is also a group of the formula VIIIa or VIIIb, and r is 1 or 2 and m is a number from 0 to 2, the sum (t.q/r)+m being equal to the coordination number of the metal ion M, and A is $H_2O$ or an amine of the formula III, in which $R_{12}$ is unsubstituted or $-OH$-substituted $C_1-C_{18}$ alkyl, $C_5-C_{12}$ cycloalkyl, $C_6-C_{18}$ aralkyl, $C_7-C_{20}$ aralkyl, a substituted or unsubstituted aminoalkyl group or a piperidinyl group and $R_{13}$ is hydrogen or unsubstituted or $-OH$-substituted $C_1-C_{18}$ alkyl, $C_5-C_{12}$ cycloalkyl, a substituted or unsubstituted aminoalkyl group or a piperidinyl group, or $R_{12}$ and $R_{13}$ together with the N atom form a pyrrolidine, piperidine or morpholine ring which is substituted by alkyl groups or is unsubstituted, and $R_{14}$ is hydrogen or unsubstituted or $-OH$-substituted $C_1-C_{18}$ alkyl.

Amongst the compounds of the formula XVI, those to be mentioned in particular are those in which M is $Ca^{2+}$, $Mn^{2+}$, $Zn^{2+}$, $Co^{2+}$, $Ni^{2+}$ or $Al^{3+}$ and q is 2 or 3 and t is 2 or 4 and $L_3$ is as defined above, and $R_{15}$ and $R_{16}$ independently of one another are hydrogen or $C_1-C_8$ alkyl, which can be unsubstituted or substituted by a group of the formulae Va, Vb or Vc; or a group Vc or a radical $-OR_{24}$, and $R_5$ is hydrogen or methyl and Y is hydrogen, $C_1-C_4$ alkyl, $C_3-C_6$ alkenyl, propargyl, $C_2-C_5$ alkoxyalkyl, benzyl, acetyl or one of the groups $-CH_2COOR_6$, $-CH_2CH(R_7)-OR_8$, $-COOR_9$ or $-CONHR_9$, in which $R_6$ is $C_1-C_4$ alkyl and $R_7$ is hydrogen or methyl and $R_8$ is hydrogen and $R_9$ is $C_1-C_4$ alkyl, and $X_1$ and $X_2$ independently of one another are $-O-$ or

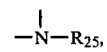

and $R_{21}$ is hydrogen or $C_1-C_4$ alkyl and $R_{22}$ and Z are as defined above, and $R_{23}$ is $C_1-C_{18}$ alkyl, allyl, propargyl, cyclohexyl, phenyl, 4-t-butylphenyl or a group of the formula VI, in which Y and $R_{21}$ are as defined, and $R_{24}$ is hydrogen or $C_1-C_{12}$ alkyl, $C_2-C_6$ alkenyl, cyclohexyl, phenyl or benzyl, which are unsubstituted or substituted by a group of the formula Vc, in which $X_2$ and $R_{23}$ are as defined, and $R_{25}$ is hydrogen, $C_1-C_{12}$ alkyl, which can be unsubstituted or substituted by a group of the formula Vc, in which $X_2$ and $R_{23}$ are as defined, or allyl, propargyl, cyclohexyl, phenyl, benzyl or a group $-CH_2-CH(R_5)-OH$, in which $R_5$ is as defined, and $R_{18}$ is a group $-N(R_{25})R_{27}$ and $R_{19}$ is hydrogen, or $R_{18}$ and $R_{19}$ together are $=O$ or $=NR_{27}$, and $R_{20}$ is hydrogen or $C_1-C_{12}$ alkyl, $C_2-C_6$ alkenyl, cyclohexyl or phenyl, which are unsubstituted or substituted by a group of the formula Vc, and, if $R_{18}$ and $R_{19}$ together are $=O$, $R_{20}$ is a group of the formula Va, and $R_{27}$ is hydrogen or $C_1-C_{12}$ alkyl, $C_2-C_6$ alkenyl, cyclohexyl or phenyl, which are unsubstituted or substituted by a group of the formula Vc; or $R_{27}$ is a group of the formula VI, and r is 1 and m is a number from 0 to 2, the sum $(2.q)+m$ being equal to the coordination number of the metal ion M, and A is $H_2O$ or an amine of the formula III, in which $R_{12}$ and $R_{13}$ independently of one another are $C_1-C_8$ alkyl, $C_1-C_6$ hydroxyalkyl or a substituted aminoalkyl group of the formula IId

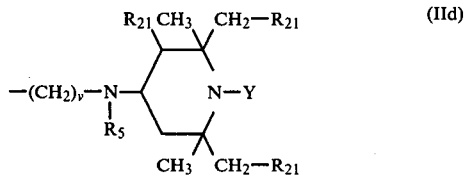

(IId)

in which v is 1 to 8 and Y, $R_5$ and $R_{21}$ are as defined, or $R_{12}$ and $R_{13}$ together form a piperidine group, and $R_{14}$ is hydrogen or $C_1-C_8$ alkyl or $C_1-C_6$ hydroxyalkyl.

Particularly preferred compounds of the formula XVI are those in which M is $Ca^{2+}$, $Zn^{2+}$ or $Ni^{2+}$ and q is 2 and L is a t-dentate group of the formula IVc, which is substituted by at least one group of the formula VI, and t is 2, and $R_{15}$ and $R_{16}$ are hydrogen and $R_{18}$ is a group $-N(R_{25})R_{27}$, in which $R_{25}$ is hydrogen, $C_1-C_{12}$ alkyl or a group $-CH_2-CH(R_5)-OH$, in which $R_5$ is hydrogen or methyl, and $R_{27}$ is hydrogen or $C_1-C_4$ alkyl substituted by a group of the formula Vc, or a group of the formula VI, and $X_2$ is $-O-$ and Y is hydrogen, methyl or acetyl and $R_{21}$ is hydrogen or methyl and $R_{23}$ is a group of the formula VI, and $R_{19}$ is hydrogen and $R_{20}$ is hydrogen or $C_1-C_4$ alkyl, and r, m, A, $R_{12}$, $R_{13}$ and $R_{14}$ are as defined above.

Pariticularly preferred compounds of the formula XVI are also those in which M is $Ca^{2+}$, $Zn^{2+}$ or $Ni^{2+}$ and q is 2 and L is a t-dentate group of the formula IVc, which is substituted by at least one group of the formulae Va or VI, and t is 2 and $R_{18}$ and $R_{19}$ together are $=O$, and $R_{15}$ is hydrogen, $C_1-C_4$ alkyl, which is unsubstituted or substituted by a group of the formulae Va or VI, or a group Vc or a radical $-OR_{24}$ and $R_{16}$ is hydrogen and $X_1$ is

and $R_{21}$ is hydrogen or methyl and Y is hydrogen, methyl or acetyl, and $R_{24}$ is $C_1-C_4$ alkyl substituted by a group of the formula Vc, and $R_{23}$ is a group of the formula VI and $X_2$ is $-O-$, and $R_{20}$ is hydrogen, $C_1-C_5$ alkyl, or $C_1-C_4$ alkyl or $C_2$ alkenyl substituted by a group of the formula Vc, or a group of the formulae Va, in which $X_2$, $R_{21}$ and Y are as defined, and $R_{25}$ is hydrogen, $C_1-C_{12}$ alkyl or a group $-CH_2-CH(R_5)-OH$, in which $R_5$ is hydrogen or methyl, and r, m, A, $R_{12}$, $R_{13}$ and $R_{14}$ are as defined above.

Particularly preferred compounds of the formula XVI are also those in which M is $Ca^{2+}$, $Zn^{2+}$ or $Ni^{2+}$ and q is 2 and L is a t-dentate group of the formula IVc, which is substituted by at least one group of the formula Va or VI, and t is 2, and $R_{18}$ and $R_{19}$ together are $=NR_{27}$, and $R_{15}$ is hydrogen, $C_1-C_4$ alkyl, which is unsubstituted or substituted by a group of the formulae Va or VI, or a group Vc or a radical $-OR_{24}$ and $R_{16}$ is hydrogen, and $X_1$ is

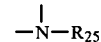

and $R_{21}$ is hydrogen or methyl and Y is hydrogen, methyl or acetyl, and $R_{24}$ is $C_1-C_4$ alkyl substituted by a group of the formula Vc, and $R_{23}$ is a group of the formula VI, and $X_2$ is $-O-$ and $R_{20}$ is hydrogen, $C_1-C_5$ alkyl or $C_1-C_4$ alkyl which is substituted by a group of the formula Vc, and $R_{25}$ is hydrogen, $C_1-C_{12}$ alkyl or a group $-CH_2-CH(R_5)-OH$, in which $R_5$ is hydrogen or methyl, and $R_{27}$ is a group of the formula VI, and r, m, A, $R_{12}$, $R_{13}$ and $R_{14}$ are as defined above.

Examples of compounds of the formula XVI are: the 1:2 $Ni^{2+}$ complex of N-methyl-N-(2-hydroxyphenyl)-N-[1',2',2',6',6'-pentamethyl-piperidin-4'-oxy-carbonyl-methyl]azomethine. (4-amino-2,2,6,6-tetramethyl-piperidine)$_2$, the 1:3 $Al^{3+}$ complex of N-phenyl-N-(2-hydroxyphenyl)-N-[2'-(1-benzyl-2,2,6,6-tetramethyl-piperidin-4-oxy-carbonyl)-phenyl]-azomethine, the 1:1 $Ni^{2+}$ complex of hexamethylene-di-{N-methyl-[2-hydroxy-5-(1',2',2',6',6'-pentamethyl-piperidin-4'-yl)]}-azomethine. (triethanolamine)$_2$, the 1:2 $Ca^{2+}$ complex of N-(1,2,2,6,6-pentamethyl-piperidin-4-yl)-N-n-butyl-N-([2'-hydroxy-5'-t-octyl]-benzyl)-amine. (dibenzyl-propylamine)$_2$, the 1:2 $Ni^{2+}$ complex of hexamethylene-di-{N-[2-hydroxy-4-(1'-hexyl-2',2',6',6'-tetramethyl-piperidin-4'-oxy-carbonylmethyl-oxy)]}-benzylamine. (triethanolamine)$_2$, the 1:2 $Mg^{2+}$ complex of 2-{1',2',2',6',6'-pentamethyl-piperidin-4-oxycarbonyl}-4-{1',2',2',6',6'-pentamethyl-piperidin-4-oxycarbonyl-methyl-oxy}-phenol. (4-dimethylamine-2,2,6,6-tetramethyl-piperidine)$_2$ and the 1:2 $Ni^{2+}$ complex of 2-methyl-carbonyl{-3,5-di-2',2',6',6'-tetramethyl-piperidin-4-oxycarbonyl-methyloxy}-phenol. (triethanolamine)$_2$.

The preparation of the compounds of the formula I is known.

Thus, the compounds of the formula I in which s and m are 0 are obtained most simply by reacting approximately one mol of the free ligand $[L]H_r$ with approximately $r/_q*$ mols of an alkali metal hydroxide, alcoholate, hydride or amide or of an alkaline earth metal hydroxide, alcoholate, hydride or amide or with $r/_{2q}*$ mols of an alkali metal carbonate or alkaline earth metal carbonate, in an inert organic solvent. The reaction can be carried out at room temperature or, in order to accelerate the conversion, at elevated temperatures up to the reflux temperature. The reaction is most simply carried out at room temperature. Alkali metals which can be used are, especially, lithium, sodium, potassium or rubidium, in particular sodium or potassium. A suitable alkaline earth metal is, especially, calcium. $q*$ defines the charge on the alkali metal cation or alkaline earth metal cation M* used. Suitable inert organic solvents are alcohols, such as methanol or ethanol, ethers, such as dioxane, tetrahydrofurane or diethyl ether, aromatic hydrocarbons, such as benzene, toluene or xylene, aliphatic hydrocarbons, such as hexane or ligroin, or amides, such as dimethylformamide or hexamethylphosphoric acid triamide.

The alkali metal salts or alkaline earth metal salts $[L]M^*_{r/q^*}$ obtained in this way can then be reacted in a simple manner with a metal salt $ML^*_q$. For this reaction, in particular, q/r mols of the compound $[L]M^*_{r/q^*}$ are employed per mol of $ML^*_q$, in an inert organic solvent. Suitable solvents are those described above. The temperature can again be chosen between room temperature and the reflux temperature. Anions suitable as the anion L* are, especially, halides, in particular chloride, or carboxylate anions, such as acetate or caproate.

It is also possible to combine the two process steps described above or to employ hydrates of the compounds described.

If, for example, a hydroxide or carbonate is used as $ML^*_q$, it is even possible to dispense with the formation of the alkali metal salts or alkaline earth metal salt.

If s is not 0, the procedure is, in principle, as described and (q−s)/r mols of a compound $[L]M^*_{r/q}$ and s mols of a compound BM* are reacted with a metal salt of the formula $ML^*_q$. The same result is achieved by means of ligand replacement reactions, for which, for example, $MB_q$ and (q−s)/r mols of $[L]M^*_{r/q}$ are employed. The compounds B are known and can be prepared by known methods.

If the compound of the formula I is to contain an amine A, the simplest procedure is to heat a solution of the compound $[M^{q+}][L^{r-}]_{(q-s)/r}·[B^-]_s$, the preparation of which has been described above, in one of the aprotic inert solvents described, in the presence of at least m mols of the compound A. The temperature can be up to the reflux temperature but in any case should be at least 30° C. Advantageous results are achieved by boiling under reflux, in which case a water separator is used.

The amines A are known and can be prepared by known methods. Some compounds of this type are described, for example, in U.S. Pat. No. 3,901,031 or, if A contains piperidyl radicals, also in German Offenlegungsschrift No. 2,349,962.

The condition which a chelate-forming ligand according to the present invention has to meet is that it contains at least one group of the formula IIa or IIb. The methods by which compounds which contain groups IIa or IIb are obtained has been described in the literature. Thus, for example, derivatives of pyrrolidine are described in German Offenlegungsschrift No. 2,459,331; derivatives of imidazolidine are described in German Offenlegungsschrift No. 2,427,853 or German Offenlegungsschrift No. 2,500,313; derivatives of 1,4-diazacycloheptanone are described in German Offenlegungsschrift No. 2,428,877 or German Offenlegungsschrift No. 2,621,924: derivatives of piperazine are described in German Offenlegungsschrift No. 2,315,042; derivatives of 1-aza-4-thiacyclohexane are described in German Offenlegungsschrift No. 1,351,865; derivatives of dipiperidyl are described in German Offenlegungsschrift No. 2,425,984 and derivatives of piperidine are described, for example, in German Offenlegungsschriften Nos. 2,258,752, 2,040,975 and 2,227,689, U.S. Pat. Nos. 3,639,409 and 3,640,928 or British Pat. No. 1,262,234.

As already mentioned, those chelate-forming agents which contain one or more piperidine radicals are of particular interest. This is also indicated by the fact that the particularly preferred compounds contain groups of the formula Va, Vb or VI, which are obtained, for example, as follows:

If the group concerned is a group of the formula Va or VI, the corresponding 4-hydroxypiperidines (known from German Offenlegungsschrift No. 2,352,658) or the 4-aminopiperidines (known from U.S. Pat. No. 3,684,765) can be used as the starting materials. The 4-OH compounds can generally be prepared from the 4-oxopiperidines of the formula XVII

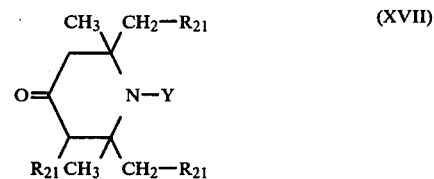

(XVII)

in which $R_{21}$ and Y are as defined above, by reduction, for example catalytic hydrogenation over Raney nickel, whilst the 4-$NH_2$ compounds are obtainable, for example, from a compound of the formula XVII by means of reductive reaction with ammonia.

The 4-oxopiperidines of the formula XVII, in which Y is hydrogen, can be prepared by various processes.

Thus, for example, the reaction of an aliphatic ketone with ammonia is described by W. Traube in Chem. Ber. 41, 777 (1908).

4-Oxopiperidines of the formula XVII in which Y is hydrogen can also be prepared analogously to the process described in U.S. Pat. No. 3,513,170. In this case, an alkyl-substituted tetrahydropyrimidine is rearranged hydrolytically in the presence of an acid catalyst.

N-H compounds of the formula XVII, which have different substituents in the 2-position and in the 6-position, can be prepared by reacting a ketone of the formula $CH_3-CO-CH_2R_{21}$ with ammonia. The pyrimidine formed is hydrolysed to an aminoketone of the formula XVIII, as described in Helv. Chim. Acta 30, 114 (1947).

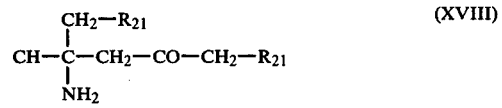

(XVIII)

In a second process step, the compounds of the formula XVIII are reacted with ammonia and a ketone $CH_3-CO-CH_2-R_{21}$, as has been described, for example, in Monatsh. Chemie 88, 464 (1957). The compounds of the formula XVII in which Y is hydrogen can be obtained by hydrolysis from the pyrimidine obtained in this way.

Compounds of the formula XVII in which Y is not hydrogen, or also those which correspond to the protonated form of the group of the formula Vb, can be prepared from the corresponding N—H compounds by substitution. The reactions involved are the substitution reactions customary for secondary amines, although, because of the steric hindrance resulting from the methyl group or the group $-CH_2-R_{21}$, these reactions proceed more slowly. N—H compounds can, for example, be reacted with alkyl halides, alkenyl halides, aralkyl halides or alkoxyalkyl halides, with dialkyl sulphates, with epichlorohydrins, with esters of chlorocarboxylic acids, such as chloroacetates, or with acid chlorides or acid anhydrides.

The group —$CH_2$—$CH(R_7)$—$OR_8$ can be introduced by reacting the N—H-piperidines with an epoxide of the formula

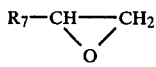

and subsequently acylating the reaction product with an acyl chloride of the formula $R_8Cl$. A hydroxyalkyl radical can be introduced analogously.

Compounds of the 2,2,6,6-tetramethyl-4-(alkoxycarbonylcyanomethyl)-piperidine type, which can be used as intermediates, are also known from British Pat. Specification No. 1,214,426.

A radical $R_{22}$ is introduced, starting from the 4-hydroxy- or 4-amino-piperidines, by conventional methods, for example by reaction with a chloride of the formula $R_{26}Cl$ or by a hydrogenolytic condensation reaction with $H_2N$—$R_{26}$.

The requirement to which the groups of the formula IIa, IIb, Va, Vb and VI, which have been described at the indicated points, are subject is that they contain a functional group, especially an amino, hydroxyl or carboxylic acid (ester) group, which makes it possible to incorporate the groups mentioned into the chelate-forming molecule by means of conventional trans-esterification or condensation reactions.

If these groups are, for example, in the substituents $R_{15}$ or $R_{16}$ as alkyl substituted by a group Va or Vb, in which Z is —O—, a hydroxyphenylalkyl chloride is reacted in a known manner with an alcohol or amine derived from the groups Va or Vb, in the presence of a base. The reaction with an alcoholate is also suitable and is known as the Williamson synthesis. If, in the formula Vb, Z is —O—C(O)—, or if $R_{15}$ or $R_{16}$ is a group of the formula Vc, in which $R_{23}$ is, for example, a radical VI, the introduction thereof is effected most simply by reacting aromatic carboxylic acids, for example benzoic acid, phenylacetic acid or β-phenylpropionic acid, with an alcohol derived from the formula Va or Vb, by means of a conventional trans-esterification reaction. This reaction can be acid-catalysed or base-catalysed. If $R_{15}$ or $R_{16}$ is an alkoxy group substituted by a radical of the formula Vc, the introduction thereof is effected, for example, by reacting a phenol, for example a procatechol, resorcinol, hydroquinone, pyrogallol or phloroglucinol, with a halogenoalkyl derivative of the group of the formula Vc in an inert solvent in the presence of a base. If $R_{15}$ or $R_{16}$ is a group of the formula VI, a phenol is reacted with a 4-oxo derivative of a group of the formula VI in the presence of an acid and the reaction product is subsequently reduced, as has also been described, for example, in U.S. Pat. No. 3,847,930.

If L is a group of the formula IVa, the preparation thereof can be effected analogously to the description in U.S. Pat. No. 2,971,941, approximately 2 mols of a phenol being reacted with 1 mol of $SCl_2$ and the radicals $R_{15}$ and $R_{16}$ being introduced as described above, before or after the $SCl_2$ stage. If $R_{15}$ is a group of the formula VI, this is introduced before the $SCl_2$ stage. The chelate-forming agents $H_2L$ corresponding to the formula IVa which are prepared in this way are novel and therefore are also a subject of the present invention. A characteristic of compounds which contain a group of the formula IVa is that r can have a value of 1 or 2. This is dependent on the ratio of the concentration in which the free ligand is employed and on the metal salt in the chelating step described above.

If L is a group of the formula IVb, this can be prepared analogously to the compounds of British Pat. No. 878,362 or British Pat. No. 1,332,560. If $R_{15}$ or $R_{16}$ contains a group IIa or IIb, or, respectively, a group Va, Vb or VI, these are introduced as described above. If $R_{17}$ is a group of the formula Vc, in which $R_{23}$ is a radical of the formula VI, the known compounds in which $R_{23}$ is alkyl are used as the starting materials and these are trans-esterified in a known manner with an alcohol derived from the group Va. If $R_{17}$ is a group of the formula —$OR_{24}$, the simplest procedure is to react the analogous compound in which $R_{17}$ is hydroxyl with a compound $ClR_{24}$. Some of the chelate-forming agents of the formula IVb are known from Japanese Published Specification No. 51-88,484.

If L is a group of the formula IVc, $R_{15}$ or $R_{16}$ are introduced as described, if these contain a group IIa or IIb or, respectively Va, Vb or VI.

If $R_{18}$ and $R_{19}$ together are =O, the starting materials used are as a rule salicyclic acid or its alkyl esters, salicylamide or an α-hydroxyphenyl ketone. The introduction of a group of the formula Va as $R_{20}$ is therefore effected, using a salicyclate as the starting material, by a simple transesterification reaction with an alcohol or amine which is derived from the formula Va. Compounds in which $R_{20}$ is an alkyl, alkenyl, cycloalkyl or aryl group substituted by a group of the formula Vc can be prepared in an analogous manner by trans-esterification. In order to obtain the compounds in which $R_{20}$ is a group of the formula VII, approximately 2 mols of a salicylate are reacted with approximately 1 mol of a diol. The desired radicals $R_{15}$ and $R_{16}$ can be incorporated, in the maner indicated above, before or after this stage. The chelate-forming agents of the formula IVc, in which $R_{18}$ and $R_{19}$ together are =O, which are thus obtained, are novel compounds and therefore are a subject of the present invention.

The chelate-forming agents of the formula IVc, in which $R_{18}$ and $R_{19}$ together are =$NR_{27}$, can be prepared in a known manner from the keto compounds thus obtained. For this purpose, the keto compounds are reacted with a primary amine in a conventional condensation reaction. The amine can be an amine which is derived from a group of the formula Va, in which $X_1$ is

or can also be an alkyl-, alkenyl-, cycloalkyl- or arylamine substituted by a group of the formula Vc. The resulting compounds of the formula IVc, in which $R_{18}$ and $R_{19}$ together with =$NR_{27}$, are novel substances and therefore are also a subject of the present invention. The compounds in which $R_{27}$ is a group of the formula VIIIb are obtained by replacing the primary amine by a diamine and allowing this to react with 2 mols of the keto compound.

The azomethine compounds of the formula IVc which have been described can be reduced to the compounds of the formula IVc in which $X_1$ is 

$$-\overset{|}{N}H$$

by known reduction processes, for example by means of hydrogen on Pd/C. Another variant is to introduce a secondary amine $HN(R_{25})R_{27}$ in a Mannich reaction in the presence of an aldehyde, preferably formaldehyde. If the chelate-forming agent contains a group of the formula VIIIa as $R_{27}$, it is prepared by reduction of the corresponding di-azomethine compound. The compounds of the formula IVc in which $R_{18}$ is $-N(R_{25})R_{27}$, which are obtained in the manner described, are novel and therefore are also a subject of the invention.

If the ligands used are those in which r=2, oligomers or even polymers can form. A characteristic of these is that they contain several centers capable of forming a chelate and therefore are able to bind several metal centres. Higher-molecular substances of this type are distinguished by an increased stability to extraction. Higher-molecular substances of this type are novel and therefore are also a subject of the invention, as is indicated, in particular, by the fact that the ratio, given in the formula I, of the metal to the ligand L is also correct in this case if it is calculated for the structural unit on which the polymer is based. The molecular weight is approximately 400–10,000 and preferably 400–2,000.

According to the present invention, the compounds of the formula I can be used as stabilisers for plastics in order to protect them against damage by the action of oxygen, heat and light. Examples of such plastics are the polymers listed on pages 12–14 of German Offenlegungsschrift No. 2,456,864.

The stabilising of polyolefines and styrene polymers and of polyurethanes is of particular importance, and the compounds of the formula I are outstandingly suitable for this. Examples of such polymers are high density and low density polyethylene, polypropylene, ethylene/propylene copolymers, polystyrene, styrene/butadiene/acrylonitril terpolymers, mixtures of polyolefines or of styrene polymers, and polyurethanes based on polyethers or polyesters, in the form of films, fibres, lacquers, elastomers or foams.

The stabilisers are added to the plastics in a concentration of 0.01 to 5% by weight, calculated relative to the material to be stabilised. Preferably, 0.03 to 1.5, and particularly preferentially 0.2 to 0.6% by weight of the compounds, calculated relative to the material to be stabilised, are incorporated into the latter.

Incorporation can be effected after polymerisation, for example by mixing the compounds and, if desired, further additives into the melt by the methods customary in the art, before or during shaping, or by applying the dissolved or dispersed compounds to the polymer, with subsequent evaporation of the solvent if necessary.

The novel compounds can also be added to the plastics to be stabilised in the form of a master batch which contains these compounds, for example in a concentration of 2.5 to 25% by weight.

In the case of crosslinked polyethylene, the compounds are added prior to crosslinking.

The invention therefore also relates to the plastics stabilised by the addition of 0.01 to 5% by weight of a compound of the formula I, which plastics can, if desired, contain yet further known and customary additives. The plastics stabilised in this way can be employed in very diverse forms, for example as films, fibres, tapes or profiles or as binders for lacquers, adhesives or putties.

Examples which may be mentioned of further additives, together with which the stabilisers which can be used according to the invention can be employed, are: antioxidants, such as simple 2,6-dialkylphenols, derivatives of alkylated hydroquinones, hydroxylated thiodiphenyl ethers, alkyldiene-bisphenols, O-, N- and S-benzyl compounds, hydroxybenzylated malonates, hydroxybenzyl-aromatic compounds, s-triazine compounds, amides of β-(3,5-di-tert.-butyl-4-hydroxyphenyl)-propionic acid, esters of β-(3,5-di-tert.-butyl-4-hydroxyphenyl)-propionic acid, esters of β-(5-tert.-butyl-4-hydroxy-3-methylphenyl)-propionic acid, esters of 3,5-di-tert.-butyl-4-hydroxyphenylacetic acid, acylaminophenols, benzylphosphonates, aminoaryl derivatives, UV absorbers and light stabilisers, such as 2-(2'-hydroxyphenyl)-benztriazoles, 2,4-bis-(2'-hydroxyphenyl)-6-alkyl-s-triazines, 2-hydroxybenzophenones, 1,3-bis-(2'-hydroxybenzoyl)-benzenes, esters of substituted or unsubstituted benzoic acids, and acrylates; and, furthermore, nickel compounds, stearically hindered amines, oxalic acid diamides, metal deactivators, phosphites, compounds which destroy peroxide, polyamide stabilisers, basic Co stabilisers, PVC stabilisers, nucleating agents or other additives, for example plasticisers, lubricants, emulsifiers, fillers, carbon black, asbestos, kaolin, talc, glass fibres, pigments, optical brighteners, flameproofing agents and antistatic agents.

Examples of further additives together with which the stabilisers which can be used according to the invention can be employed are given on pages 18–24 of German Offenlegungsschrift No. 2,427,853.

The preparation and use of the compounds according to the invention are described in more detail in the examples which follow.

EXAMPLE 1

137.2 g (0.5 mol) of N-[2-hydroxybenzyl]-N-methyl-N-[2,2,6,6-tetramethyl-piperidyl-4]-amine were dissolved in 200 ml of ethanol and a solution of 11.5 g of Na in 300 ml of ethanol was added dropwise at room temperature in the course of 1.5 hours and the mixture was stirred for a further 1.5 hours at 50° C. 59.4 g of $NiCl_2.2H_2O$, dissolved in 300 ml of ethanol, were added dropwise in the course of 2 hours and the solution was then kept under reflux for 2 hours. The solvent was evaporated, the residue was taken up in hot hexane and the NaCl was filtered off. After cooling the hexane solution, the stabiliser 1 crystallised out as a green-yellow coloured compound.

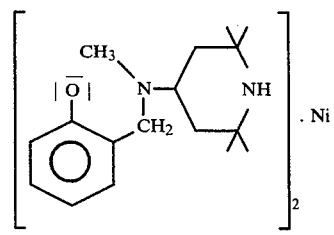

Ni calculated (relative to $H_2O$): 9.26%.
Ni found: 9.67%.

found (relative to H₂O): 4.5%.

The following compounds were prepared analogously to compound I.

and 1.36 g of sodium ethylate were added under a nitrogen atmosphere. The reaction mixture was stirred at room temperature for 20 minutes and 1.65 g of NiCl₂.2-

| Example | Stabiliser | Ni calculated (relative to H₂O %) | Ni found % | H₂O % |
|---|---|---|---|---|
| 2 | 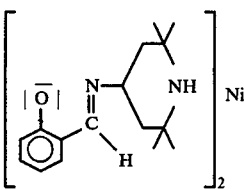 | 10.00 | 9.2 | 1.3 |
| 3 | 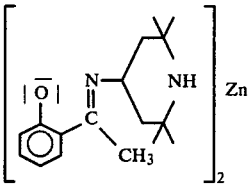 | 10.26 | 9.9 | 3.9 |
| 4 | 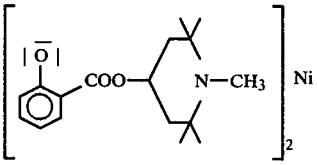 | 9.14 | 8.57 | 0.6 |
| 5 | 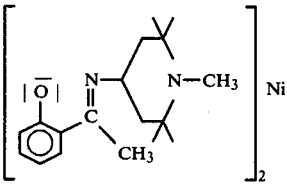 | 8.8 | 7.96 | 4.2 |
| 6 | 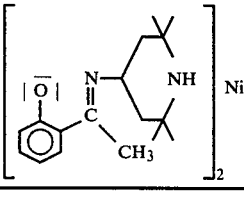 | 9.7 | 9.67 | 4.4 |

EXAMPLE 7

15.66 g of di-{2-hydroxy-5-t-octyl-3-[N-methyl-N-(2,2,6,6-tetramethylpiperidinyl-4)-aminomethyl]-phenyl} sulphide were dissolved in 100 ml of ethanol H₂O, dissolved in 40 ml of ethanol, were then added dropwise. The mixture was stirred at 24° C. for 12 hours. The NaCl which had precipitated was filtered off and the solvent was evaporated. The 16.9 g of the pale green stabiliser 7.

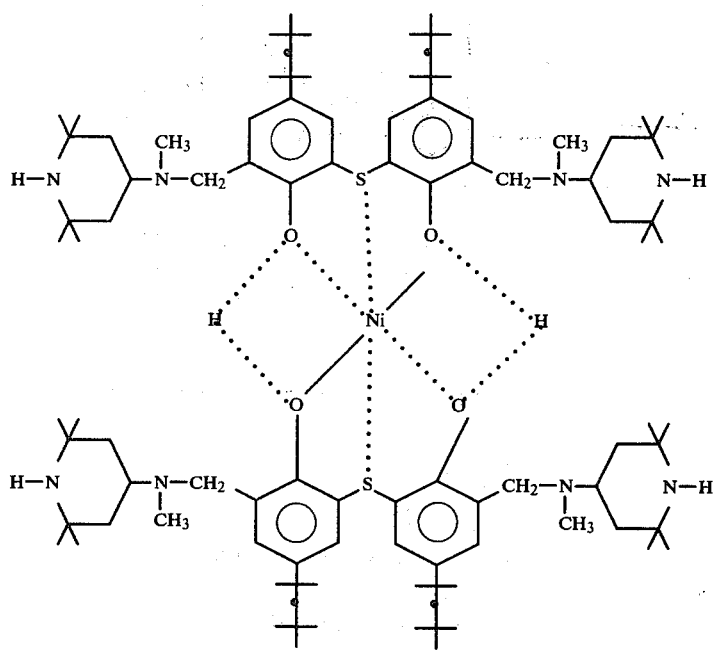

Stabiliser 7 thus obtained, gave the following analysis:
$C_{100}H_{170}N_8O_4S_2.Ni.2H_0$
Ni calculated (relative to $H_2O$): 3.51%.
Ni found: 3.43%.

EXAMPLE 8

12.6 g [0.02 mol] of the Ni salt of N-methyl-N-[2,2,6,6-tetramethyl-piperidinyl-4-]-amine and 4 g (0.02 mol) of N,N-dimethyl-N-[1,2,2,6,6-pentamethylpiperidyl-4]-amine were dissolved in 200 ml of toluene and the solution was kept under reflux for 7 hours using a water separator. The solvent was then evaporated off, the residue was taken up in hot hexane and, after the solution had cooled, the crystals formed were filtered off and dried in a vacuum oven at 60° C. for 20 hours. The product

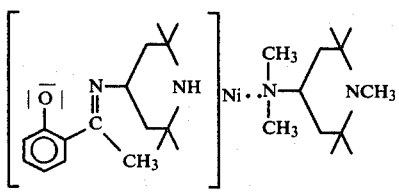

Stabiliser 8 gave the following analysis:
Ni calculated (relative to $H_2O$): 7.03%.
Ni found: 7.65%.

The compounds of the following types were prepared analogously to stabiliser 8:

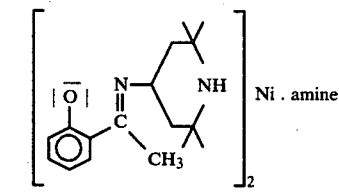

The corresponding ligands A, used as amines, are listed in the examples in the table which follows.

| Example | Amine A | Ni calculated (relative to $H_2O$) % | Ni found % | $H_2O$ % |
|---|---|---|---|---|
| 9 | HN—C4H9 (on tetramethylpiperidine NH) | 6.9 | 6.69 | 3.7 |
| 10 | CH3—N—CH2CH2—N—CH3 (bis tetramethyl-N-CH3-piperidinyl) | 5.69 | 6.13 | 3.0 |
| 11 | HN—CH2CH2—NH (bis tetramethylpiperidinyl NH) | 6.03 | 6.45 | 2.9 |

The following compounds were prepared analogously to the stabiliser according to Example 8

[structure: Zn·amine complex with salicylaldimine ligand bearing tetramethylpiperidine group, as shown]

| Ex. | Amine A | (a) Ni calculated (b) N calculated (relative to H₂O) % | (a) Ni found (b) N found % | H₂O % |
|---|---|---|---|---|
| 12 | CH₃-N(CH₃)- tetramethylpiperidine N-CH₃ | (a) 7.86 | (a) 7.09 | 2.6 |
| 13 | NH-CH₂CH₂-NH bis-tetramethylpiperidine (NH) | (a) 6.73 (b) 11.54 | (a) 5.78 (b) 11.4 | 2.1 |
| 14 | CH₃-N-CH₂CH₂-N-CH₃ bis-tetramethylpiperidine (N-CH₃) | (a) 6.36 | (a) 5.76 | 2.1 |
| 15 | HO-CH₂CH₂\N/CH₂CH₂OH tetramethylpiperidine N-CH₂CH₂-OH | (a) 7.51 (b) 9.66 | (a) 5.85 (b) 9.13 | 2.03 |

The following compounds were prepared analogously to the stabiliser according to Example 8:

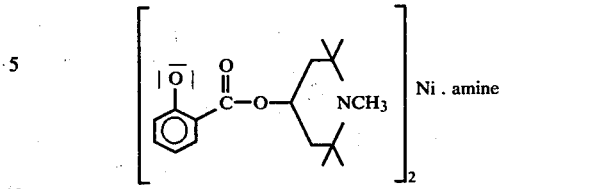

| Ex. | Amin A | Ni calculated (relative to H₂O) % | Ni found % | H₂O % |
|---|---|---|---|---|
| 16 | NHC₄H₉ tetramethylpiperidine (NH) | 6.89 | 6.51 | 0.5 |
| 17 | H₃C-HN-CH₂CH₂-N-H-CH₃ bis-tetramethylpiperidine (N-CH₃) | 4.61 | 5.11 | <0.3 |
| 18 | HN-CH₂CH₂-N-H bis-tetramethylpiperidine (NH) | 5.98 | 5.29 | 0.6 |

EXAMPLE 19

(a) 22.1 g of 3,3'-di-(t-octyl)-6,6'-diphenylsulphide and 26.8 g of 4-n-octylamino-2,2,6,6-tetramethyl-piperidine were dissolved in 100 ml of ethanol; and 8.6 g of a 35% solution of formaldehyde were then added dropwise at 23° C. under nitrogen. The reaction mixture was maintained for 4 hours at reflux temperature, and the solvent was subsequently evaporated off under vacuum to yield 35.2 g of di-{2-hydroxy-5-t-octyl-3-[N-octyl-N-(2,2,6,6-tetramethylpiperidyl-4)-aminomethyl]phenyl}-sulphide.

(b) 20.08 g of the product from Example 19a were treated analogously to Example 5 with sodium ethanolate (from 0.92 g of Na in 20 ml of ethanol) and 3.3 g of NiCl₂·2H₂O. The resulting product: 21.3 g of Stabiliser 19

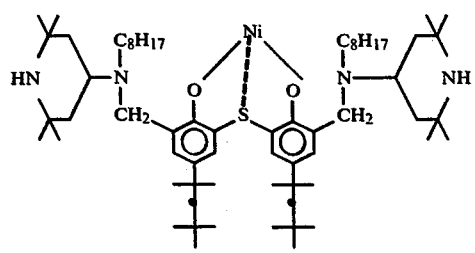

gave the following analysis values: C₆₄H₁₁₂N₄O₂S·Ni·2-H₂O:
Ni (calculated): 5.35%.

Ni (found): 5.1%.

EXAMPLE 20

13.3 g of Stabiliser 19 were taken up in 150 ml of ethanol, and 1.87 g of 4-amino-2,2,6,6-tetramethyl-piperidine in 20 ml of ethanol were added dropwise at 24° C. in a nitrogen atmosphere; the reaction solution was subsequently stirred for 16 hours. The solvent was then evaporated off to leave 15.0 g of green crystals (Stabiliser 20),

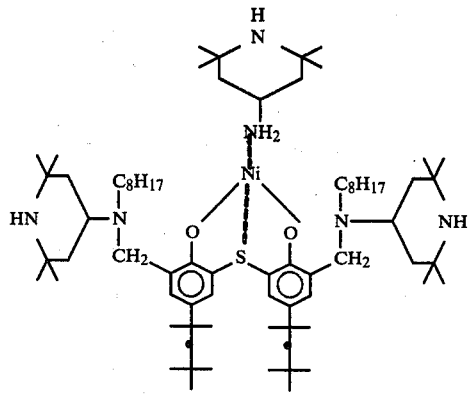

which gave the following analysis values:
Ni (calculated): 4.83%.
Ni (found): 4.54%.

EXAMPLE 21

Freshly prepared sodium methylate (from 1.15 g of Na and 40 ml of methanol) was added to 19.7 g of (N-[2-hydroxy-4-t-octylbenzyl]-N-methyl-N-[2,2,6,6-tetramethyl-piperidinyl-4]-amine in 150 ml of methanol. After the mixture had been stirred for ½ hour, 4.3 g of $NiCl_2.2H_2O$ in 50 ml of methanol were added dropwise, and stirring was continued for 5 hours at 24° C. The sodium was filtered off and the solvent evaporated off. The resulting greenish-brown residue

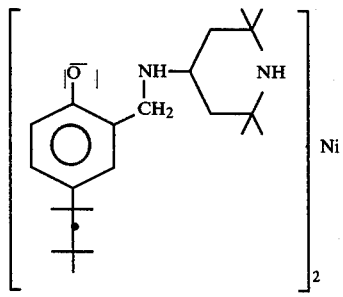

(Stabiliser 21) gave the following analysis values:
Ni (calculated): 7.04%.
Ni (found): 7.28%.

EXAMPLE 22

52.5 g (0.1 mol) of N-[2-hydroxybenzyl]-N-[2,2,6,6-tetramethyl-piperidyl-4]-amine were dissolved in 250 ml of methanol, and 100 ml of a 1 molar sodium methylate solution were added. To this solution were then added dropwise at room temperature, in the course of ½ hour, 25 ml of a 2 molar solution of anhydrous nickel chloride in methanol (corresponding to 0.05 mol of $NiCl_2$), and the reaction mixture was refluxed for 30 minutes. The sodium chloride which had precipitated was filtered off, and the filtrate was evaporated to dryness. The residue was extracted with ether at room temperature, the extract was concentrated by evaporation, and dried at 80° C. under a pressure of 11 mm Hg to yield a dark beige powder of the following composition:

(Stabiliser 22)

| Ni | (calculated) | 10.10 % | Ni | (found) | 10.03 % |
|---|---|---|---|---|---|
| C | " | 66.10 % | C | " | 65.94 % |
| H | " | 8.67 % | H | " | 8.85 % |
| N | " | 9.63 % | N | " | 9.71 % . |

EXAMPLE 23

52.5 g (0.1 mol) of N-[2-hydroxybenzyl]-N-[2,2,6,6-tetramethyl-piperidyl-4]-amine were dissolved in 250 ml of absolute ethanol, and to the solution were added 100 ml of a 1 molar sodium methylate solution. A solution of 6.81 g (0.05 mol) of anhydrous zinc chloride in 20 ml of absolute methanol was added dropwise to the above solution; the mixture was refluxed for 1½ hours, and the solvent was subsequently evaporated off. The residue was then extracted with hot toluene; the extract was concentrated by evaporation and dried at 60° C. under a pressure of 11 mm Hg. There was obtained a yellowish powder of the following composition:

Stabilizer 23

| Zn | (calculated) | 11.11 % | Zn | (found) | 10.5/10.4 % |
|---|---|---|---|---|---|
| C | " | 65.35 % | C | " | 64.42/64.39 % |
| H | " | 8.57 % | H | " | 8.76/8.56 % |
| N | " | 9.53 % | N | " | 9.07/9.14 % . |

EXAMPLE 24

Light-stabilising effect in high-pressure polyethylene sheets 100 parts of polyethylene granules of low density (=0.917) were homogenised with 0.05 part of a stabiliser given in the following Table in a Brabender plastograph for 10 minutes at 180° C. The mixture thus obtained was removed as quickly as possible from the kneader, and pressed in a toggle press to give a 2–3 mm thick sheet. A portion of the resulting pressed blank was cut out and pressed between two high-gloss hard aluminium sheets, using a manually operated hydraulic laboratory press, for 6 minutes at 170° C. under a pressure of 12 tons to obtain a 0.1 mm thick sheet, which was immediately chilled in cold water. Specimens each 60×44 mm were then punched from this sheet and exposed in the Xenotest 1200. These test specimens were removed from the exposure apparatus at regular intervals and their carbonyl content was tested in an IR spectrophotometer. The increase in the carbonyl extinction on exposure is a measure of the photooxidative degradation of the polymer (see L. Balaban et al., J. Polymer Sci., Part C, 22, 1059–1071 (1969); J. F. Heacock, J. Polymer Sci., Part A-1, 22, 2921–34 (1969) and D. J. Carlsson and D. M. Wiles, Macromolecules 2, 587–606 (1969), and from experience this increase is associated with a deterioration of the mechanical properties of the polymer. The time taken to reach a carbonyl extinction of 0.100 is taken as a measure of the protective action of the stabiliser used.

The results are summarised in Table I.

TABLE I

| Stabiliser | Exposure time in hours until the carbonyl extinction is 0.1 |
|---|---|
| none | 270 h |
| No. 3 | 1630 h |
| No. 10 | 1630 h |
| No. 12 | 2100 h |
| No. 11 | 1800 h |

EXAMPLE 25

100 parts of polypropylene powder (melt index 1.5 g/10 min., 230° C., 2160 g load) were mixed in a drum mixer with 0.1 part of pentaerythritol-tetrakis-[3-(3,5-di-tert-butyl-4-hydroxyphenyl)-propionate] and 0.15 part of one of the stabilisers listed in the following Table II, and the mixture was extruded in an extruder at 200°–220° C. and granulated. The granules were then processed in the customary manner by means of an extruder with a slot die into the form of sheets; these were subsequently cut into ribbons and then stretched at elevated temperature to six times their original length. The denier of these ribbons was 700–900 den., their width 4 mm and their tensile strength 5.5–6.5 g/den. These ribbons were exposed in a Xenotest 1200. Specimens were subjected at regular intervals to a tensile elongation test, by which was shown that a progressive decrease in the tensile strength was occurring with increasing exposure time. The exposure time until the tensile strength has decreased to half its initial value is lengthened by the action of the light stabilisers.

TABLE II

| Stabiliser No. | Exposure time in the Xenotest 1200 until the tensile strength has decreased to half the initial value |
|---|---|
| none | 400 h |
| 14 | 2300 h |
| 16 | 2030 h |
| 20 | 3950 h |
| 12 | 2100 h |
| 11 | >2000 h |
| 10 | 3080 h |
| 15 | 2100 h |
| 8 | 2050 h |
| 9 | 910 h |
| 5 | 3680 h |

EXAMPLE 26

Light stabilising effect in PP fibres (130/37)

1000 parts of unstabilised polypropylene powder (melt index ~18) were mixed in a drum mixer with 1 part of pentaerythritoltetrakis-[3-(3,5-di-tert-butyl-4-hydroxyphenyl)-propionate] and with 3 parts of one of the light stabilisers shown in the following Table III; and the mixture was subsequently extruded in an extruder at 220° C. and granulated. The granules obtained were spun in a laboratory melt spinning machine at a maximum temperature of 270° C. at a speed of 300 meters per minute to produce a 130/37 denier multifilament. This was stretched and twisted by means of a draw twister. The stretching ratio was 1:5.6 and the twist number was 15/meter, so that finally multifilaments 130/37 denier were obtained. These multifilaments were mounted on white cardboard and exposed in the Xenotest 1200. The exposure time until there occurred a 50% loss of tensile strength was taken as a measure of the protective action of the stabiliser.

The results are summarised in Table III.

TABLE III

| Stabiliser No. | Exposure time in the Xenotest 1200 until the tensile strength has decreased to half the initial value |
|---|---|
| none | 250 h |
| 3 | 500 h |
| 4 | 1400 h |
| 6 | 825 h |

What is claimed is:

1. A composition comprising plastics subject to thermal, oxidative and light degradation stabilized with an effective stabilizing amount of a metal complex of the formula I

$$(M^{q\oplus})(L^{r\ominus})_{(q-s)/r}(B^{63})_s \cdot mA \qquad (I)$$

in which M is a metal ion having a double or triple positive charge selected from the group consisting of $Mg^{2+}$, $Ca^{2+}$, $Sr^{2+}$, $Ba^{2+}$, $Zn^{2+}$, $Cd^{2+}$, $Al^{3+}$, $Sn^{2+}$, $Cr^{3+}$, $Co^{2+}$, $Ni^{2+}$, $VO^{2+}$, $MoO^{2+}$, $(R)_2 Sn^{2+}$, and $(CH_2CH_2COOR)_2 Sn^{2+}$, wherein R is $C_1$–$C_8$ Alkyl, q is 2 or 3; $L^{r\ominus}$ is a 2-, or 3- or 4-dentate chelate-forming agent selected from the category consisting of the groups IVa, IVb and IVc

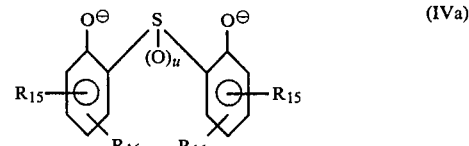

(IVa)

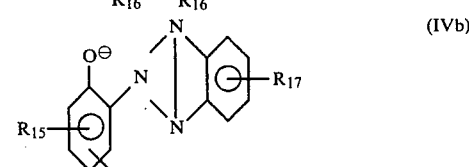

(IVb)

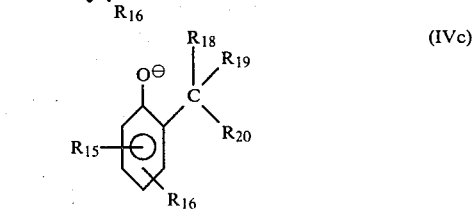

(IVc)

in which u is 0 or 1 and $R_{15}$ and $R_{16}$ independently of one another are hydrogen, $C_1$-$C_{18}$ alkyl, which can be unsubstituted or substituted by a group Va, Vb or Vc:

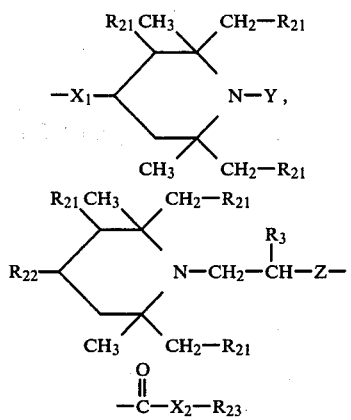

or a group Vc, or a group of the formula VI

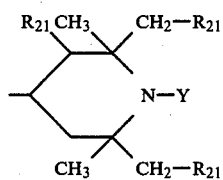

in the p-position, or halogen or a radical —$OR_{24}$, or $R_{15}$ and $R_{16}$ together are a 1,3-butadiene-1,4-diyl radical, and $R_5$ is hydrogen, methyl or phenyl and Y is hydrogen, oxyl, alkyl, alkenyl, alkynyl, alkoxyalkyl, aralkyl, 2,3-epoxypropyl, formyl, acetyl, acryloyl, crotonyl, or one of the groups —$CH_2COOR_6$, —$CH_2$—$CH(R_7)$—$OR_8$, —$COOR_9$ or —$CONHR_9$, in which $R_6$ is alkyl, alkenyl, phenyl, aralkyl or cycloalkyl and $R_7$ is hydrogen, methyl or phenyl and $R_8$ is hydrogen, formyl, acetyl, propionyl, butyryl, octanoyl, dodecanoyl, stearoyl, acryloyl, benzoyl, cinnamoyl, phenylacetyl, phenylproprionyl or each of benzyl, cinnamoyl, phenylacetyl or phenylproprionyl substituted by chlorine, alkyl, alkoxy and/or hydroxyl, and $R_9$ is alkyl, cyclohexyl, phenyl or benzyl, and $X_1$ and $X_2$ independently of one another are —O— or

and $R_{21}$ is hydrogen or $C_1$-$C_8$ alkyl and $R_{22}$ is hydrogen or a group —$X_1R_{26}$, and Z is —O— or

and $R_{23}$ is $C_1$-$C_{18}$ alkyl, $C_3$-$C_6$ alkenyl, $C_3$-$C_4$ alkynyl, $C_5$-$C_7$ cycloalkyl, $C_6$-$C_{10}$ aryl, $C_7$-$C_{14}$ aralkyl, $C_7$-$C_{14}$ alkylphenyl or a group of the formula VI, and $R_{24}$ is hydrogen or $C_1$-$C_8$ alkyl, $C_5$-$C_7$ cycloalkyl, $C_6$-$C_{14}$ aryl, $C_7$-$C_{14}$ aralkyl or $C_2$-$C_{12}$ alkenyl which are unsubstituted or substituted by a group of the formula Vc; or $R_{24}$ is formyl, acetyl, propionyl, butyryl, octanoyl, dodecanoyl, stearoyl, acryloyl, benzoyl, cinnamoyl, phenylacetyl, phenylpropionyl, or each of benzoyl, cinnamoyl, phenylacetyl or phenylpropionyl substituted by chlorine, $C_1$-$C_8$ alkyl, $C_1$-$C_8$ alkoxy, as group Vc or hydroxyl, and $R_{25}$ is hydrogen, or $C_1$-$C_{18}$ alkyl, or $C_3$-$C_6$ alkenyl, $C_3$-$C_4$ alkynyl, $C_5$-$C_7$ cycloalkyl, $C_6$-$C_{10}$ aryl, $C_7$-$C_{14}$ aralkyl, a group of the formula $CH_2$—$CH(R_5)$—$OR_{26}$ or a group of the formula VI, and $R_{26}$ is hydrogen, $C_1$-$C_{18}$ alkyl, $C_3$-$C_6$ alkenyl, cyclohexyl, benzyl or formyl, acetyl, propionyl, butyryl, octanoyl, dodecanoyl, stearoyl, acryloyl, benzoyl, cinnamoyl, phenylacetyl, phenylpropionyl, or each of benzoyl, cinnamoyl, phenylacetyl or phenylpropionyl substituted by chlorine, $C_1$-$C_8$ alkyl, $C_1$-$C_8$ akkoxy or hydroxyl, and $R_{17}$ is hydrogen, $C_1$-$C_{18}$ alkyl, halogen, a group —$OR_{24}$ or a group of the formula Vc and $R_{18}$ is a group —$N(R_{25})R_{27}$ and $R_{19}$ is hydrogen, or $R_{18}$ and $R_{19}$ together are =O or =$NR_{27}$, and $R_{20}$ is hydrogen, $C_7$-$C_{14}$ aralkyl, $C_7$-$C_{14}$ alkylphenyl, or $C_1$-$C_{18}$ alkyl, $C_2$-$C_{12}$ alkenyl, $C_5$-$C_{12}$ cycloalkyl or $C_6$-$C_{14}$ aryl, which are unsubstituted or substituted by a group of the formula Vc, or, if $R_{18}$ and $R_{19}$ together are =O, $R_{20}$ is a group of the formula Va; or $R_{20}$ is also a group of the formula VII

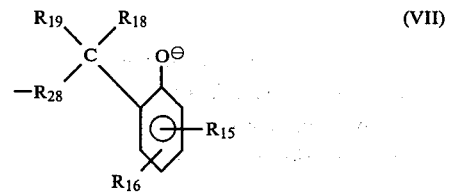

in which $R_{15}$, $R_{16}$, $R_{18}$ and $R_{19}$ are as defined above and $R_{28}$ is $C_1$-$C_{12}$ alkylene, butenylene, $C_6$-$C_{10}$ arylene or diphenylene, and $R_{27}$ is hydrogen, $C_7$-$C_{14}$ aralkyl, $C_7$-$C_{14}$ alkylphenyl, hydroxyl, or $C_1$-$C_{18}$ alkyl, $C_2$-$C_{12}$ alkenyl, $C_5$-$C_{12}$ cycloalkyl or $C_6$-$C_{14}$ aryl, which are unsubstituted or substituted by a group of the formula Vc, or a group of the formula VI or a group of the formula —$CH_2$—$CH(R_5)$-$OR_{26}$; or, if $R_{20}$ is not a group of the formula VII, $R_{27}$ is also a group of the formulae VIIIa or VIIIb

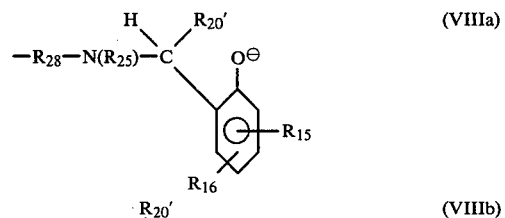

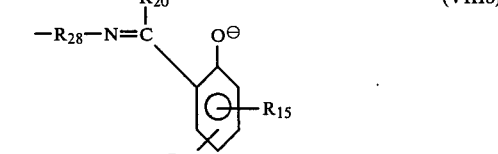

in which R'$_{20}$ has the meaning defined for $R_{20}$ with the exception of the groups of the formula VII, and $R_{15}$, $R_{16}$, $R_{25}$ and $R_{28}$ are as defined above, and r is 1 or 2, equal to the number of coordinatively bonded phenolate anions in the molecule, B, as an anion having a single charge, is an anion of an aliphatic or aromatic carboxylic acid, of a phosphonic acid half-ester, of a phosphinic acid, of a phosphinous acid or of an enol of the formula IX

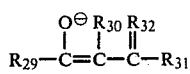
(IX)

in which R29 is alkyl, alkenyl, cycloalkyl, aralkyl or aryl and R30 is hydrogen, alkyl, alkenyl, cycloalkyl, aralkyl, aryl or alkoxycarbonyl, or R29 and R30 together 1,4-butadi-1,3-enylene or 1,4-butylene, and R31 is alkyl, alkenyl, cycloalkyl, aralkyl, aryl or alkoxy, or amino, and R32 is oxo or imino, and the sum $(q-s)/r+s$ must equal q, and m is an integer from 0 to 3, the sum $t((q-s/r))+s+m$ being equal to the coordination number of the metal ion M, and A is H$_2$O or an amine of the formula III

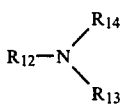
(III)

in which R12 is alkyl, hydroxyalkyl, or optionally alkyl-substituted cycloalkyl, aryl or aralkyl, or aminoalkyl which may be substituted by a piperidinyl group, or R12 is a piperidinyl group, and R13 is hydrogen, alkyl, hydroxyalkyl, or optionally alkyl-substituted cycloalkyl or aminoalkyl which may be substituted by a piperidinyl group or R13 is a piperidinyl group; or R12 and R13 together with the N atoms form a pyrrolidine, piperidine or morpholine group which may be alkyl-substituted and R14 is hydrogen, alkyl or hydroxyalkyl.

2. A compound

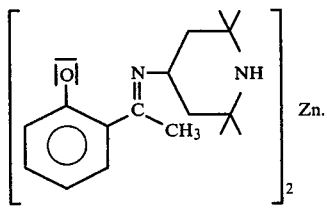

3. A compound

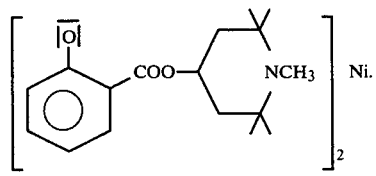

4. A metal complex of the formula XIV

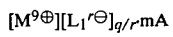
(XIV)

in which M is mg$^{2+}$, VO$^{2+}$, Ca$^{2+}$, Zn$^{2+}$, Co$^{2+}$, Ni$^{2+}$ or Al$^{3+}$ and q is 2 or 3 and L$_1$ is a t-dentate group of the formula IV

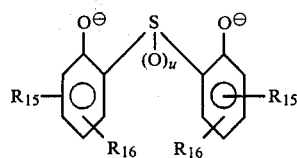
(IVa)

which is substituted by at least one group of the formulae Va, Vb or VI,

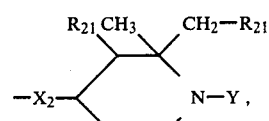
(Va)

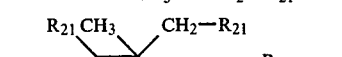
(Vb)

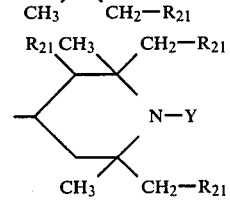
(VI)

and u is 0, 1 and t is 3, and R15 and R16 independently of one another are hydrogen or C$_1$-C$_{18}$ alkyl which can be unsubstituted or substituted by a group of the formulae Va, Vb or Vc;

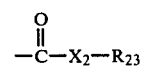
(Vc)

or a group Vc, or a group of the formula VI in the p-position, halogen or a radical —OR24, or R15 and R16 together form a 1,3-butadiene-1,4-diyl radical, and R5 is hydrogen, methyl or phenyl and Y is hydrogen, oxyl, C$_1$-C$_{12}$ alkyl, C$_3$-C$_{12}$ alkenyl, C$_3$-C$_6$ alkynyl, C$_2$-C$_{21}$ alkoxyalkyl, C$_7$-C$_9$ aralkyl, 2,3-epoxypropyl, formyl, acetyl, acryloyl, crotonyl, or one of the groups —CH$_2$COOR$_6$, —CH$_2$—CH(R$_7$)—OR$_8$, —COOR$_9$ or —CONHR$_9$, in which R$_6$ is C$_1$-C$_{12}$ alkyl, C$_3$-C$_6$ alkenyl, phenyl, C$_7$-C$_8$ aralkyl or cyclohexyl and R$_7$ is hydrogen, methyl or phenyl and R$_8$ is hydrogen, formyl, acetyl, propionyl, butyryl, octanoyl, dodecanoyl, stearoyl, acryloyl, benzoyl, cinnamoyl, phenylacetyl, phenylpropionyl, or each of benzoyl, cinnamoyl, phenylacetyl or phenylpropionyl substituted by chlorine, C$_1$-C$_4$ alkyl, C$_1$-C$_8$ alkoxy or hydroxyl, and R$_9$ is C$_1$-C$_{12}$ alkyl, cyclohexyl, phenyl or benzyl, and X$_1$ and X$_2$ independently of one another are —O— or

and R21 is hydrogen or C$_1$-C$_8$ alkyl and R22 is hydrogen or a group —X$_1$R$_{26}$ and Z is —O— or

and $R_{23}$ is $C_1$-$C_{18}$ alkyl, $C_3$-$C_6$ alkenyl, $C_3$-$C_4$ alkynyl, $C_5$-$C_7$ cycloalkyl, $C_6$-$C_{10}$ aryl, $C_7$-$C_{14}$ aralkyl, $C_7$-$C_{14}$ alkylphenyl or a group of the formula VI, in which Y and $R_{21}$ are as defined, and $R_{24}$ is hydrogen or $C_1$-$C_8$ alkyl, $C_5$-$C_7$ cycloalkyl, $C_6$-$C_{14}$ aryl, $C_7$-$C_{14}$ aralkyl or $C_2$-$C_{12}$ alkenyl which are unsubstituted or substituted by a group of the formula Vc, in which $X_2$ and $R_{23}$ are as defined, or is formyl, acetyl, propionyl, butyryl, octanoyl, dodecanoyl, stearoyl, acryloyl, benzoyl, cinnamoyl, phenylacetyl, phenylpropionyl, or each of benzoyl, cinnamoyl, phenylacetyl or phenylpropionyl substituted by chlorine, $C_1$-$C_8$ alkyl, $C_1$-$C_8$ alkoxy, a group Vc or hydroxyl, $R_{25}$ is hydrogen, $C_1$-$C_{18}$ alkyl, which can be unsubstituted or substituted by a group of the formula Vc, in which $X_2$ and $R_{23}$ are as defined, or $C_3$-$C_6$ alkenyl, $C_3$-$C_4$ alkynyl, $C_5$-$C_7$ cycloalkyl, $C_6$-$C_{10}$ aryl, $C_7$-$C_{14}$ aralkyl, a group of the formula $CH_2$—$CH(R_5)$—$OR_{26}$ or a group of the formula VI, and $R_{26}$ is hydrogen, $C_1$-$C_{18}$ alkyl, $C_3$-$C_6$ alkenyl, cyclohexyl, benzyl or formyl, acetyl, propionyl, butyryl, octanoyl, dodecanoyl, stearoyl, acryloyl, benzoyl, cinnamoyl, phenylacetyl, phenylpropionyl, or each of benzoyl, cinnamoyl, phenylacetyl or phenylpropionyl substituted by chlorine, $C_1$-$C_8$ alkyl, $C_1$-$C_8$ alkoxy or hydroxyl, and r is 1 or 2 and m is a number from 0 to 3, the sum $(3.q/r)+m$ being equal to the coordination number of the metal ion M, and A is $H_2O$ or an amine of the formula III,

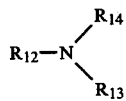

in which $R_{12}$ is unsubstituted or —OH— substituted $C_1$-$C_{18}$ alkyl, $C_5$-$C_{12}$ cycloalkyl, $C_6$-$C_{18}$ aryl, $C_7$-$C_{20}$ aralkyl, a aminoalkyl group or a piperidinyl group, and $R_{13}$ is hydrogen or unsubstituted or —OH-substituted $C_1$-$C_{18}$ alkyl, $C_5$-$C_{12}$ cycloalkyl, aminoalkyl group or a piperidinyl group, or $R_{12}$ and $R_{13}$ together with the N atom form a pyrrolidine, piperidine or morpholine ring which is substituted by alkyl groups or is unsubstituted and $R_{14}$ is hydrogen or unsubstituted or —OH—substituted $C_1$-$C_{18}$ alkyl.

5. A metal complex of the formula XV $$[M^{7\oplus}][L_2{}^{r\ominus}]_{q/r}mA \qquad (XV)$$

in which M is $Mg^{2+}$, $Sr^{2+}$, $VO^{2+}$, $Ca^{2+}$, $Mn^{2+}$, $Zn^{2+}$, $Co^{2+}$, $Ni^{2+}$ or $Al^{3+}$ and q is 2 or 3 and $L_2$ is a t-dentate group of the formula IVb

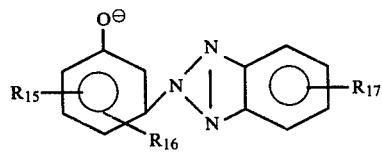

which is substituted by at least one group of the formulae Va, Vb or VI,

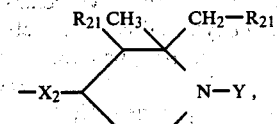

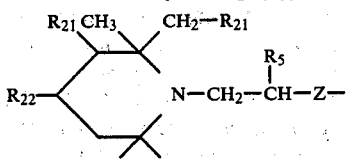

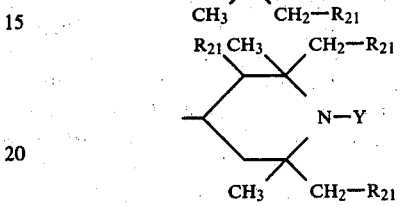

and t is 2, and $R_{15}$ and $R_{16}$ independently of one another are hydrogen, $C_1$-$C_{18}$ alkyl, which can be unsubstituted or substituted by a group of the formulae Va, Vb or Vc,

or a group Vc, or a group of the formula Vi in the p-position, halogen or a radical —$OR_{24}$, or $R_{15}$ and $R_{16}$ together form a 1,3-butadiene-1,4-diyl radical, and $R_5$ is hydrogen, methyl or phenyl and Y is hydrogen, oxyl, $C_1$-$C_{12}$ alkyl, $C_3$-$C_{12}$ alkenyl, $C_3$-$C_6$ alkynyl, $C_2$-$C_{21}$ alkoxyalkyl, $C_7$-$C_9$ aralkyl, 2,3-epoxypropyl, formyl, acetyl, acryloyl, crotonyl, or one of the groups —$CH_2COOR_6$, —$CH_2$—$CH(R_7)$—$OR_8$, —$COOR_9$ or —$CONHR_9$, in which $R_6$ is $C_1$-$C_{12}$ alkyl, $C_3$-$C_6$ alkenyl, phenyl, $C_7$-$C_8$ aralkyl or cyclohexyl and $R_7$ is hydrogen, methyl or phenyl and $R_8$ is hydrogen, formyl, acetyl, propionyl, butyryl, octanoyl, dodecanoyl, stearoyl, acryloyl, benzoyl, cinnamoyl, phenylacetyl, phenylpropionyl, or each of benzoyl, cinnamoyl, phenylacetyl or phenylpropionyl substituted by chlorine, $C_1$-$C_4$ alkyl, $C_1$-$C_8$ alkoxy or hydroxyl, and $R_9$ is $C_1$-$C_{12}$ alkyl, cyclohexyl, phenyl or benzyl, and $X_1$ and $X_2$ independently of one another are —O— or

and $R_{21}$ is hydrogen or $C_1$-$C_8$ alkyl and $R_{22}$ is hydrogen or a group -$X_1R_{26}$ and Z is —O— or

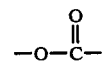

and $R_{23}$ is $C_1$-$C_{18}$ alkyl, $C_3$-$C_6$ alkenyl, $C_3$-$C_4$ alkynyl, $C_5$-$C_7$ cycloalkyl, $C_6$-$C_{10}$ aryl, $C_7$-$C_{14}$ aralkyl, $C_7$-$C_{14}$ alkylphenyl or a group of the formula VI, in which Y and $R_{21}$ are as defined, and $R_{24}$ is hydrogen or $C_1$-$C_8$ alkyl, $C_5$-$C_7$ cycloalkyl, $C_6$-$C_{14}$ aryl, $C_7$-$C_{14}$ aralkyl or $C_2$-$C_{12}$ alkenyl which are unsubstituted or substituted by a group of the formula Vc, in which $X_2$ and $R_{23}$ are as defined, or is formyl, acetyl, propionyl, butyryl, octanoyl, dodecanoyl, stearoyl, acryloyl, benzoyl, cinnamoyl, phenylacetyl, phenylpropionyl, or each of benzoyl, cinnamoyl, phenylacetyl or phenylpropionyl substituted by chlorine, $C_1$-$C_8$ alkyl, $C_1$-$C_8$ alkoxy, a group Vc or hydroxyl, $R_{25}$ is hydrogen, $C_1$-$C_{18}$ alkyl, which can be unsubstituted or substituted by a group of the formula Vc, in which $X_2$ and $R_{23}$ are as defined, or $C_3$-$C_6$ alkenyl, $C_3$-$C_4$ alkynyl, $C_5$-$C_7$ cycloalkyl, $C_6$-$C_{10}$ aryl, $C_7$-$C_{14}$ aralkyl, a group of the formula $CH_2$—$CH(R_5)$—$OR_{26}$ or a group of the formula VI, and $R_{26}$ is hydrogen, $C_1$-$C_{18}$ alkyl, $C_3$-$C_6$ alkenyl, cyclohexyl, benzyl or formyl, acetyl, propionyl, butyryl, octanoyl, dodecanoyl, stearoyl, acryloyl, benzoyl, cinnamoyl, phenylacetyl, phenylpropionyl, or each of benzoyl, cinnamoyl, phenylacetyl or phenylpropionyl substituted by chlorine, $C_1$-$C_8$ alkyl, $C_1$-$C_8$ alkoxy or hydroxyl, and $R_{17}$ is hydrogen, $C_1$-$C_{18}$ alkyl, halogen, a group —$OR_{24}$, or a group of the formula Vc in which $R_{23}$, $R_{24}$ and $X_2$ are as defined, and r is 1 and m is an integer from 0 to 2, the sum (2q)+m being equal to the coordination number of the metal ion M, and A is $H_2O$ or an amine of the formula III,

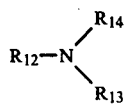
(III)

in which $R_{12}$ is unsubstituted or —OH-substituted $C_1$-$C_{18}$ alkyl, $C_5$-$C_{12}$ cycloalkyl, $C_6$-$C_{18}$ aryl, $C_7$-$C_{20}$ aralkyl, a aminoalkyl group or a piperidinyl group and $R_{13}$ is hydrogen or unsubstituted or —OH-substituted $C_1$-$C_{18}$ alkyl, $C_5$-$C_{12}$ cycloalkyl, a aminoalkyl group or a piperidinyl group, or $R_{12}$ and $R_{13}$ together with the N atom form a pyrrolidine, piperidine or morpholine ring which is substituted by alkyl groups or is unsubstituted, and $R_{14}$ is hydrogen or unsubstituted or —OH-substituted $C_1$-$C_{18}$ alkyl.

6. A composition comprising plastics subject to thermal, oxidative and light degradation stabilized with from 0.01 to 5% of a compound according to claim 5.

7. A process for stabilizing plastics against thermal, oxidative and light degradation which comprises incorporating into said plastics from 0.01% to 5% of a compound according to claim 4.

8. A process of stabilizing plastics against thermal, oxidative and light degradtion which comprises incorporating into said plastics from 0.01 to 5% of a compound according to claim 5.

9. A composition of matter comprising a plastics subject to thermal, oxidative and light degradation stabilized with from 0.01 to 5% of a compound according to claim 4.

10. A process of stabilizing a plastics against thermal, oxidative on light degradation which comprises incorporating into said polymeric material from 0.01 to 5% of a compound according to claim 5.

* * * * *

UNITED STATES PATENT AND TRADEMARK OFFICE
CERTIFICATE OF CORRECTION

PATENT NO. : 4,263,202
DATED : APRIL 21, 1981
INVENTOR(S) : MICHAEL RASBERGER, SAMUEL EVANS AND PAUL MOSER

It is certified that error appears in the above—identified patent and that said Letters Patent is hereby corrected as shown below:

CLAIM 1, column 36, line 36 reads:

$(M^{9\oplus})(L^{r\ominus})\ldots$"

should read:

$(M^{q\oplus})(L^{r\ominus})\ldots$"

CLAIM 1, column 37, line 14 reads:

should read:

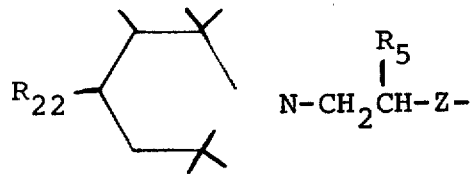

UNITED STATES PATENT AND TRADEMARK OFFICE
CERTIFICATE OF CORRECTION

PATENT NO. : 4,263,202  PAGE 2 of 4
DATED : APRIL 21, 1981
INVENTOR(S) : MICHAEL RASBERGER, SAMUEL EVANS AND PAUL MOSER

It is certified that error appears in the above—identified patent and that said Letters Patent is hereby corrected as shown below:

CLAIM 4, column 39, line 63 reads:

"$[M^{9\oplus}][L_1^{r\ominus}]\ldots$"

should read:

"$[M^{q\oplus}][L_1^{r\ominus}]\ldots$"

CLAIM 4, column 39, line 65 reads:

"in which M is $mg^{2+}$, $VO^{2+}$, $Ca^{2+}$, $Zn^{2+}$, $Co^{2+}$, $Ni^{2+}$"

should read:

"in which M is $Mg^{2+}$, $VO^{2+}$, $Ca^{2+}$, $Mn^{2+}$, $Zn^{2+}$, $Co^{2+}$, $Ni^{2+}$"

UNITED STATES PATENT AND TRADEMARK OFFICE
CERTIFICATE OF CORRECTION

PATENT NO. : 4,263,202
DATED : APRIL 21, 1981
INVENTOR(S) : MICHAEL RASBERGER, SAMUEL EVANS AND PAUL MOSER

It is certified that error appears in the above—identified patent and that said Letters Patent is hereby corrected as shown below:

CLAIM 4, column 40, Line 16 reads:

" 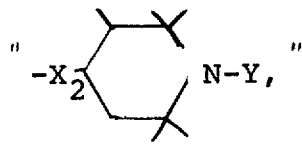 "

should read:

" 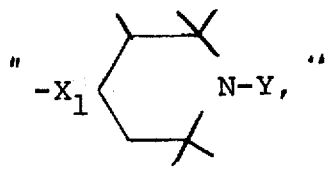 "

CLAIM 5, column 41, Line 53 reads:

$[M^7 \oplus][L_2{}^r \ominus] \ldots$ "

should read:

$[M^q \oplus][L_2{}^r \ominus] \ldots$ "

UNITED STATES PATENT AND TRADEMARK OFFICE
CERTIFICATE OF CORRECTION

PATENT NO. : 4,263,202
DATED : APRIL 21, 1981
INVENTOR(S) : MICHAEL RASBERGER, SAMUEL EVANS AND PAUL MOSER

It is certified that error appears in the above—identified patent and that said Letters Patent is hereby corrected as shown below:

CLAIM 5, column 42, line 5 reads:

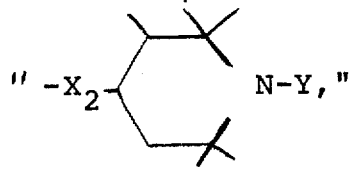

should read:

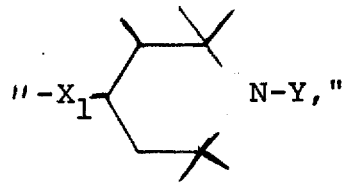

Signed and Sealed this

Eighth Day of December 1981

|SEAL|

Attest:

GERALD J. MOSSINGHOFF

Attesting Officer — Commissioner of Patents and Trademarks